(12) United States Patent
Loria et al.

(10) Patent No.: US 7,208,303 B2
(45) Date of Patent: Apr. 24, 2007

(54) BACTERIAL NITRIC OXIDE SYNTHASES AND USES THEREOF

(75) Inventors: Rosemary Loria, Ithaca, NY (US); Brian Crane, Ithaca, NY (US); Johan Kers, Ithaca, NY (US); Donna M. Gibson, Ithaca, NY (US); Michael J. Wach, Ithaca, NY (US)

(73) Assignees: Cornell Research Foundation, Inc., Ithaca, NY (US); United States of America as represented by the Secretary of Agriculture, Washington, DC (US)

( * ) Notice: Subject to any disclaimer, the term of this patent is extended or adjusted under 35 U.S.C. 154(b) by 62 days.

(21) Appl. No.: 10/858,706

(22) Filed: Jun. 2, 2004

(65) Prior Publication Data

US 2005/0042645 A1 Feb. 24, 2005

Related U.S. Application Data

(60) Provisional application No. 60/475,111, filed on Jun. 2, 2003.

(51) Int. Cl.
*C12N 9/06* (2006.01)
*C12N 5/00* (2006.01)
*C12N 1/20* (2006.01)
*C12N 1/00* (2006.01)
*C12N 5/04* (2006.01)
*C07H 21/04* (2006.01)
*C12P 21/06* (2006.01)

(52) U.S. Cl. .................. 435/191; 435/6; 435/69.1; 435/320.1; 435/325; 435/252.3; 435/254.2; 435/254.11; 435/348; 435/252.31; 435/252.32; 435/252.33; 435/252.35; 435/254.21; 435/254.3; 435/254.5; 435/419; 536/23.2

(58) Field of Classification Search ............ 435/320.1, 435/252.1, 325, 252.3, 183, 69.1, 455, 471, 435/191, 6; 536/23.2
See application file for complete search history.

(56) References Cited

OTHER PUBLICATIONS

Adak et al., "Direct Evidence for Nitric Oxide Production by a Nitric-oxide Synthase-like Protein from *Bacillus subtilis*," *J. Biol. Chem.* 277 (18):16167-16171 (2002).
Alderton et al., "Nitric Oxide Synthases: Structure, Function and Inhibition," *Biochem. J.* 357:593-615 (2001).
Alvarez et al., "Peroxynitrite-Dependent Tryptophan Nitration," *Chem. Res. Toxicol.* 9:390-396 (1996).
Carter et al., "Direct Biochemical Nitration in the Biosynthesis of Dioxapyrrolomycin. A Unique Mechanism for the Introduction of Nitro Groups in Microbial Products," *J. Chem. Soc., Chem. Commun.* 17:1271-1273 (1989).
GenBank Accession No. AAC52356 (Jan. 17, 1996).
GenBank Accession No. AAP29327 (Apr. 30, 2003).
GenBank Accession No. AAP12306 (May 16, 2003).
GenBank Accession No. AE016749 (Jan. 1, 2003).
GenBank Accession No. AE002088 (Nov. 22, 1999).
GenBank Accession No. AY204507 (May 7, 2004).
GenBank Accession No. AY204508 (May 7, 2004).
GenBank Accession No. AY204509 (May 7, 2004).
GenBank Accession No. AAO53225 (May 7, 2004).
GenBank Accession No. AAO53226 (May 7, 2004).
GenBank Accession No. AAO53227 (May 7, 2004).
GenBank Accession No. BAB04542 (Dec. 1, 2004).
GenBank Accession No. BAB95720 (Nov. 30, 2004).
GenBank Accession No. BAC69241 (Oct. 29, 2004).
GenBank Accession No. CAB12592 (Jul. 7, 2003).
Healy et al., "Involvement of a Cytochrome P450 Monooxygenase in Thaxtomin A Biosynthesis by *Streptomyces acidiscabies*," *J. Bacteriology* 184(7):2019-2029 (2002).
Hughes, M.N., "Relationships Between Nitric Oxide, Nitroxyl Ion, Nitrosonium Cation and Peroxynitrite," *Biochim. Biophys. Acta* 1411:263-272 (1999).
Jalal et al., "Structure of Anticancer Antibiotic L-Alanosine," *Acta Cryst.* C42:733-738 (1986).
Kers et al., "Nitration of a Peptide Phytotoxin by Bacterial Nitric Oxide Synthase," *Nature* 429(6987)79-82 (2004).
Koppenol, W.H., "The Basic Chemistry of Nitrogen Monoxide and Peroxynitrite," *Free Radic. Biol. Med.* 25(4-5):385-391 (1998).
Ohba et al., "Nitropeptin, A New Dipeptide Antibiotic Possessing a Nitro Group," *J. Antibiot.* 40(5):709-713 (1987).
Pant et al., "Structure of a Nitric Oxide Synthase Heme Protein from *Bacillus subtilis*," *Biochemistry* 41:11071-11079 (2002).
Patel et al., "Biological Aspects of Reactive Nitrogen Species," *Biochim. Biophys. Acta* 1411(2-3):385-400 (1999).
Ridd, J.W., "Some Unconventional Pathways in Aromatic Nitration," *Acta Chemica. Scand.* 52:11-22 (1998).

*Primary Examiner*—Rebecca E. Prouty
*Assistant Examiner*—Ganapathirama Raghu
(74) *Attorney, Agent, or Firm*—Nixon Peabody LLP

(57) ABSTRACT

The present invention relates to isolated nucleic acid molecules encoding nitric oxide synthases. The isolated nucleic acid molecules and their encoded protein or polypeptides are useful in methods for attaching a nitrogen group to a target moiety of a compound and for synthesizing a nitrogen-modified compound in a transgenic host cell. The present invention also relates to expression systems and host cells containing the nucleic acids of the present invention, as well as a method of recombinantly producing the nitric oxide synthases of the present invention.

18 Claims, 7 Drawing Sheets

FIG. 1 a b c

```
                                                      1                                                50
         Bacillus anthracis (SEQ ID NO:51)    (1)  --------------------------------------------------
            Bacillus cereus (SEQ ID NO:52)    (1)  --------------------------------------------------
      Staphylococcus aureus (SEQ ID NO:53)    (1)  --------------------------------------------------
  Staphylococcus epidermidis (SEQ ID NO:54)   (1)  --------------------------------------------------
         Bacillus halodurans (SEQ ID NO:55)   (1)  --------------------------------------------------
            Bacillus subtilis (SEQ ID NO:56)  (1)  --------------------------------------------------
      Deinococcus radiodurans (SEQ ID NO:57)  (1)  --------------------------------------------------
    Streptomyces acidiscabies (SEQ ID NO:2)   (1)  ----------------------------------------------MTSE
        Streptomyces scabies (SEQ ID NO:4)    (1)  ----------------------------------------------MTSE
   Streptomyces turgidiscabies (SEQ ID NO:6)  (1)  ----------------------------------------------MTFE
       Streptomyces avermitilis (SEQ ID NO:58) (1) LADAPPESAASRPGGDARDRHGAPSRARGWSTETWCAPHGRKDTAGESEH
                 Mus musculus (SEQ ID NO:59)   (1)  ----------------------------------QYVRIKNWGSGEI 51                                               100
         Bacillus anthracis (SEQ ID NO:51)    (1)  ---------------------------------MSKTKQLIEEASH
            Bacillus cereus (SEQ ID NO:52)    (1)  ---------------------------------MSKTKQLIEEASN
      Staphylococcus aureus (SEQ ID NO:53)    (1)  ------------------------------------MLFKEAQA
  Staphylococcus epidermidis (SEQ ID NO:54)   (1)  ---------------------------------------MLIDKARS
         Bacillus halodurans (SEQ ID NO:55)   (1)  -------------------------------MEEKERLQLEAES
            Bacillus subtilis (SEQ ID NO:56)  (1)  --------------------------------------------------
      Deinococcus radiodurans (SEQ ID NO:57)  (1)  ----------------------------MSCPAAAVLTPDMRA
    Streptomyces acidiscabies (SEQ ID NO:2)   (5)  VALGPSLPAPSPTACPALGPDSSLGP--VPSAEPATPQSCGVADPNEAEE
        Streptomyces scabies (SEQ ID NO:4)    (5)  VALGPSLPAPSPTACPALGPDSSLGP--VPSAEPATPQSCGVADPNEAEE
   Streptomyces turgidiscabies (SEQ ID NO:6)  (5)  VALGPSLPAPSPTACPALAHDSPLSP--VPSAEPATSQDCGVADPDEAEE
       Streptomyces avermitilis (SEQ ID NO:58) (51) RPPGPTLPGARGWGAARTRGDRPDGHPDHPTGSPTTDGPARPARPDRREE
                 Mus musculus (SEQ ID NO:59)  (14) LHDTLHHKATSDFTCKSKSCLGSIMNPKSLTRGPRDKPTPLEELLPHAIE 101                                              150
         Bacillus anthracis (SEQ ID NO:51)   (14)  FITICYKELS---------------------KEHFIEERMKEIQAEIE
            Bacillus cereus (SEQ ID NO:52)   (14)  FITICYKELH---------------------KEQLIEERIKEIQIEIE
      Staphylococcus aureus (SEQ ID NO:53)    (9)  FIENMYKECHY--------------------ETQIINKRLHDIELEIK
  Staphylococcus epidermidis (SEQ ID NO:54)   (9)  FIQTMYSELKY--------------------NTNEIENRMKEIEQEIN
         Bacillus halodurans (SEQ ID NO:55)  (14)  FLTKCYEELG---------------------STGELSKRLEEVRKEID
            Bacillus subtilis (SEQ ID NO:56)  (1)  -------------------------------MKDRLADIKSEID
      Deinococcus radiodurans (SEQ ID NO:57) (16)  FLRRFHEEMGE--------------------PG-LPARLRAVE
    Streptomyces acidiscabies (SEQ ID NO:2)  (53)  FLRQFHAEQSD--------------------QPVPLARRLEQVRAAID
        Streptomyces scabies (SEQ ID NO:4)   (53)  FLRQFHAEQSD--------------------QPVPLARRLEQVRAAID
   Streptomyces turgidiscabies (SEQ ID NO:6) (53)  FLRQFHAEQSD--------------------QAVPLTRRLDQVRAAID
       Streptomyces avermitilis (SEQ ID NO:58)(101) GDGHDGHEGQDGHDGHDLLCAATAFLTLHHTEERLGDPARRIAAAHAEIA
                 Mus musculus (SEQ ID NO:59) (64)  FINQYYGSFKEA-------------------KIEEHLARLEAVTKEIE 151                                              200
         Bacillus anthracis (SEQ ID NO:51)   (41)  KTGTYEHTFEELVHGSRMAWRNSNRCIGRLFWSKMHILDAREVNDEEGVY
            Bacillus cereus (SEQ ID NO:52)   (41)  KTGTYEHTFEELVHGSRMAWRNSNRCIGRLFWSKMHILDAREVNDEEGVY
      Staphylococcus aureus (SEQ ID NO:53)   (37)  ETGTYTHTEEELIYGAKMAWRNSNRCIGRLFWDSLNVIDARDVTDEASFL
  Staphylococcus epidermidis (SEQ ID NO:54)  (37)  LTGSYTHTYEELSYGAKMAWRNSNRCIGRLFWNSLNVKDARDVCDEKEFI
         Bacillus halodurans (SEQ ID NO:55)  (41)  KTGTYVHTTKELAHGARMAWRNSNRCIGRLFWESLHVLDCRHLQTEEEMA
            Bacillus subtilis (SEQ ID NO:56) (14)  LTGSYVHTKEELEHGAKMAWRNSNRCIGRLFWNSLNVIDRRDVRTKEEVR
      Deinococcus radiodurans (SEQ ID NO:57) (38)  EAGLWWPTSAELTWGAKVAWRNSTRCVGRLYWEALSVRDLRELNTAQAVY
    Streptomyces acidiscabies (SEQ ID NO:2)  (81)  ATGTYRHTTAELVYGARVAWRNSSRCIGRLYWNSLRVLDRRDATAPDEIH
        Streptomyces scabies (SEQ ID NO:4)   (81)  ATGTYRHTTAELVYGARVAWRNSSRCIGRLYWNSLRVLDRRDATAPDEIH
   Streptomyces turgidiscabies (SEQ ID NO:6) (81)  ATGTYRHTTAELVFGARVAWRNSSRCIGRLYWNSLRVLDRRDTTAPEVIH
       Streptomyces avermitilis (SEQ ID NO:58)(151) ETGTYRHTTEELVFGARVAWRNANRCIGRLYWHSLCVRDRRDVRDAKDVA
                 Mus musculus (SEQ ID NO:59) (93)  TTGTYQLTLDELIFATKMAWRNAPRCIGRIQWSNLQVFDARNCSTAQEMF 201                                              250
         Bacillus anthracis (SEQ ID NO:51)   (91)  HALIHHIKYATNDGKVKPTITIFKQYQGEENNIRIYNHQLIRYAGYKTEM
            Bacillus cereus (SEQ ID NO:52)   (91)  NALIHHIKYATNDGKVKPTITIFKQYQGEENNIRIYNHQLIRYAGYKTET
      Staphylococcus aureus (SEQ ID NO:53)   (87)  SSITYHITQATNEGKLKPYITIYAP----KDGPKIFNNQLIRYAGYDN--
  Staphylococcus epidermidis (SEQ ID NO:54)  (87)  KFIHTHIKEATNGGKIKPYITIFSP----EDTPKIYNNQLIRYAGYEN--
         Bacillus halodurans (SEQ ID NO:55)  (91)  EALVDHITYATNDGKILPTISVFRPRHPNKGDVRIWNQQLIRYAGYEEGD
            Bacillus subtilis (SEQ ID NO:56) (64)  DALFHHIETATNNGKIRPTITIFPPEEKGEKQVEIWNHQLIRYAGYESDG
      Deinococcus radiodurans (SEQ ID NO:57) (88)  EALLQHLDDAFCGGHIRPVISVFG------PGVRLHNPQLIRYA------
    Streptomyces acidiscabies (SEQ ID NO:2) (131)  RHLCTHLRQATNGGIRPVISVFAPDSPGRPGPQVWNEQLIRYAGYRRDD
        Streptomyces scabies (SEQ ID NO:4)  (131)  RHLCTHLRQATNGGIRPVISVFAPDSPGRPGPQVWNEQLIRYAGYRRDD
   Streptomyces turgidiscabies (SEQ ID NO:6)(131)  RHLCTHLRQATNGGIRPVISVFAPDAPSRPGPRVWNEQLVRYAGHRRDD
       Streptomyces avermitilis (SEQ ID NO:58)(201) EASADHLREATRDGRIRALITVFAPDAPGRPGPRIWNEQLIRYAGYARPG
                 Mus musculus (SEQ ID NO:59)(143)  QHICRHILYATNNGNIRSAITVFPQRSDGKHDFRLWNSQLIRYAGYQMPD
```

FIG. 6A

```
                                              251                                                300
     Bacillus anthracis (SEQ ID NO:51)  (141) -GVTGDSHSTAFTDFCQELGWQG-EGTNFDVLPLVFSID-GKAPIYKEIP
        Bacillus cereus (SEQ ID NO:52)  (141) -GVIGDSHSATFTDFCQGLGWQG-EGTNFDVLPLVFSIN-GKAPTYKEIP
  Staphylococcus aureus (SEQ ID NO:53)  (131) ---CGDPAEKEVTRLANHLGWKG-KGTNFDVLPLIYQLP-NESVKFYEYP
Staphylococcus epidermidis (SEQ ID NO:54) (131) ---VGDPSEKKVTRLAEHLGWKG-KGSNFDILPLIYQLP-NDTIKIHELP
     Bacillus halodurans (SEQ ID NO:55) (141) -QVIGDPISTKFTQACERLGWSG-ERTPFDVLPLVIQDG-SKPPKWFAVP
       Bacillus subtilis (SEQ ID NO:56) (114) -ERIGDPASCSLTAACEELGWRG-ERTDFDLLPLIFRMKGDEQPVWYELP
   Deinococcus radiodurans (SEQ ID NO:57)(126) ----DDPINADFVDKLRRFGWQP-RGERFEVLPLLIEVNG--RAELFSLP
Streptomyces acidiscabies (SEQ ID NO:2)  (181) GTVLGDPRTADLTEAILRLGWQGCPQGPFDVLPLVIDTPDD-KPRFFELP
     Streptomyces scabies (SEQ ID NO:4)  (181) GTVLGDPRTADLTEAILRLGWQGCPQGPFDVLPLVIDTPDD-KPRFFELP
Streptomyces turgidiscabies (SEQ ID NO:6)(181) GTVLGDPRSADLTEAIRGLGWQGGRQGPFDVLPLVIDAHDD-KPRFFELP
   Streptomyces avermitilis (SEQ ID NO:58)(251)GAVTGDPRNAGLTALARRLGWPGGPGSPFDVLPLIVQSAGD-RPRWFTLP
             Mus musculus (SEQ ID NO:59) (193) GTIRGDAATLEFTQLCIDLGWKP-RYGRFDVLPLVLQAD-GQDPEVFEIP 301                                                350
     Bacillus anthracis (SEQ ID NO:51)  (188) KEEVKEVPIEHPEYPISS-LGAKWYGVPMISDMRLEIGGISYTAAPFNGW
        Bacillus cereus (SEQ ID NO:52)  (188) REEVKEVPIEHPEYPISS-LGVKWYGVPMISDMRLEIGGISYTAAPFNGW
  Staphylococcus aureus (SEQ ID NO:53)  (176) TSLIKEVPIEHNHYPKLRKLNLKWYAVPIISNMDLKIGGIVYPTAPFNGW
Staphylococcus epidermidis (SEQ ID NO:54) (176) NDIVKEVSIHHEHYPKLSKLGLKWYAVPIISNMDLKIGGITYPTAPFNGW
     Bacillus halodurans (SEQ ID NO:55) (188) NESVKEVPLRHPEYEWFAGFQLKWYAVPIVSNMRLEIGGIHYPAAPFNGW
       Bacillus subtilis (SEQ ID NO:56) (162) RSLVIEVPITHPDIEAFSDLELKWYGVPIISDMKLEVGGIHYNAAPFNGW
   Deinococcus radiodurans (SEQ ID NO:57)(169) PQAVQEVAITHPVCLGIGELGLRWHALPVISDMHLDIGGLHLPCA-FSGW
Streptomyces acidiscabies (SEQ ID NO:2)  (230) RELVLEVPITHPDVPRLAELGLRWHAVPVISNMRLRIGGMDYPLAPFNGW
     Streptomyces scabies (SEQ ID NO:4)  (230) RELVLEVPITHPDVPRLAELGLRWHAVPVISNMRLRIGGMDYPLAPFNGW
Streptomyces turgidiscabies (SEQ ID NO:6)(230) REVVLEVPITHPDVPRLAELCLRWHAVPVISNMRLRIGGVDYPLAPFNGW
   Streptomyces avermitilis (SEQ ID NO:58)(300)EDAVLEVALTHPEYPWWRSLGLRWHAVPALAGMCLESGGICYPAAPFNGW
             Mus musculus (SEQ ID NO:59) (241) PDLVLEVTMEHPKYEWFQELGLKWYALPAVANMLLEVGGLEFPACPFNGW 351                                                400
     Bacillus anthracis (SEQ ID NO:51)  (237) YMGTEIGARNLADHDRYNLLPAVAEMMDLDTSRNGTLWKDKALIELNVAV
        Bacillus cereus (SEQ ID NO:52)  (237) YMGTEIGARNLADHDRYNLLPAVAEMMDLDTSRNGTLWKDKALIELNIAV
  Staphylococcus aureus (SEQ ID NO:53)  (226) YMVTEIGVRNFIDDYRYNLLEKVADAFEFDTLKNNSFNKDRALVELNYAV
Staphylococcus epidermidis (SEQ ID NO:54) (226) YMVTEIAVRNFTDIYRYNLLEKVAEAFEFDTLKNNSFNKDRALVELNHAV
     Bacillus halodurans (SEQ ID NO:55) (238) YMGTEIGARNLADEDRYNILPKMAEYMGLSTGKDSTLWKDKALVELNVAI
       Bacillus subtilis (SEQ ID NO:56) (212) YMGTEIGARNLADEKRYDKLKKVASVIGIAADYNTDLWKDQALVELNKAV
   Deinococcus radiodurans (SEQ ID NO:57)(218) YVQTEIAARDLADVGRYDQLPAVARALGLDTSRERTLWRDRALVELNVAV
Streptomyces acidiscabies (SEQ ID NO:2)  (280) YMGTEIGARNLVDEDRYNMLPAVAACLQLDTTSESTLWRDRALVELNVAV
     Streptomyces scabies (SEQ ID NO:4)  (280) YMGTEIGARNLVDEDRYNMLPAVAACLQLDTTSESTLWRDRALVELNVAV
Streptomyces turgidiscabies (SEQ ID NO:6)(280) YMGTEIGVRNLVDEARYNLLPAVAACLQLDTTSESTLWRDRALVELNVAV
   Streptomyces avermitilis (SEQ ID NO:58)(350)YMGTEIGARNLADADRYDLLPHLADRLGLDTRSDRSLWKDRALVELNRSV
             Mus musculus (SEQ ID NO:59) (291) YMGTEIGVRDFCDTQRYNILEEVGRRMGLETHTLASLWKDRAVTEINVAV 401                                                450
     Bacillus anthracis (SEQ ID NO:51)  (287) LHSFKKQGVSIVDHHTAAQQFQQFEKQEAACGRVVTGNWVWLIPPLSPAT
        Bacillus cereus (SEQ ID NO:52)  (287) LHSFKKQGVSIVDHHTAAQQFQQFEKQEAACGRVVTGNWVWLIPPLSPAT
  Staphylococcus aureus (SEQ ID NO:53)  (276) YHSFKKEGVSIVDHLTAAKQFELFERNEAQQGRQVTGKWSWLAPPLSPTL
Staphylococcus epidermidis (SEQ ID NO:54) (276) YHSFKADGVSIVDHLTAAKQFEMFERNEHQQNRNVTGKWSWLAPPLSPTL
     Bacillus halodurans (SEQ ID NO:55) (288) LYSYKQEGVSIVDHHTAAKQFARFEQAEQAANRKVTGRWSWLIPPVSPAT
       Bacillus subtilis (SEQ ID NO:56) (262) LHSYKKQGVSIVDHHTAASQFKRFEEQEEEAGRKLTGDWTWLIPPISPAA
   Deinococcus radiodurans (SEQ ID NO:57)(268) LHSFDAAGVKLADHHTVTAHHVRFEEREARAGREVRGKWSWLVPPLSPAT
Streptomyces acidiscabies (SEQ ID NO:2)  (330) LHSFEAAGVRISDHHEESRRFLAHLAKEERQGRTVSADWSWIVPPLSGGI
     Streptomyces scabies (SEQ ID NO:4)  (330) LHSFEAAGVRISDHHEESRRFLAHLAKEERQGRTVSADWSWIVPPLSGGI
Streptomyces turgidiscabies (SEQ ID NO:6)(330) LHSFAAAGVRISDHHEESRRFLAHLTKEERQGRTVPADWSWIVPPLSSGI
   Streptomyces avermitilis (SEQ ID NO:58)(400)LHSFDRAGVTVTDHHTESLRFLTHLDREERKGRRVGADWSWIVPPISGSA
             Mus musculus (SEQ ID NO:59) (341) LHSFQKQNVTIMDHHTASESFMKHMQNEYRARGGCPADWIWLVPPVSGSI 451                           489
     Bacillus anthracis (SEQ ID NO:51)  (337) THIYHKPYPNEILKPNFFHK------------------
        Bacillus cereus (SEQ ID NO:52)  (337) THIYHKPYPNEILKPNFFHK------------------
  Staphylococcus aureus (SEQ ID NO:53)  (326) TSNYHHGYDNTVKDPNFFYKKKESNANQCPFHH-----
Staphylococcus epidermidis (SEQ ID NO:54) (326) TSNYHHGYDNTMHHTNFFYKKEEP--MKCPFH-------
     Bacillus halodurans (SEQ ID NO:55) (338) THIFHHEYEDETVLPNYFYQPAPYESDTF---------
       Bacillus subtilis (SEQ ID NO:56) (312) THIFHRSYDNSIVKPNYFYQDKPYEB-TT-M-FF-RM--
   Deinococcus radiodurans (SEQ ID NO:57)(318) TPLWSRRYRAREESPRFVRARCPFHTPTVHASTGHAPTG
Streptomyces acidiscabies (SEQ ID NO:2)  (380) TPVFHRYYDNVDQRPNFYPHQ-----------------
     Streptomyces scabies (SEQ ID NO:4)  (380) TPVFHRYYDNVDQRPNFYPHQ-----------------
Streptomyces turgidiscabies (SEQ ID NO:6)(380) TPVFHRYYDNADQRPNFYPHQ-----------------
   Streptomyces avermitilis (SEQ ID NO:58)(450)TPVFHRTYETVERHPAYVHHPEALARARGEIDEILV---
             Mus musculus (SEQ ID NO:59) (391) TPVFHQEMLNYVLSPFYYYQIEPWKTHIWQNEK------
```

FIG. 6B

BACTERIAL NITRIC OXIDE SYNTHASES AND USES THEREOF

This application claims the benefit of U.S. Provisional Patent Application Ser. No. 60/475,111, filed Jun. 2, 2003.

The subject matter of this application was made with support from the United States Government under USDA Grant No. 99-35303-8084. The U.S. Government may have certain rights.

FIELD OF THE INVENTION

The present invention relates to isolated nucleic acid molecules encoding nitric oxide synthases, the encoded isolated nitric oxide synthases, and the uses of these isolated nucleic acids and nitric oxide synthases for catalyzing nitration and nitrosylation reactions.

BACKGROUND OF THE INVENTION

Nitric oxide synthases ("NOSs") are highly regulated enzymes that synthesize the potent cytotoxin and signal molecule nitric oxide (NO) from L-arginine (L-arg) (Alderton et al., *Biochem J.* 357:593–615 (2001)). In mammals, NOSs are responsible for many functions that range from protection against pathogens and tumor cells to blood pressure regulation and nerve transmission. The production of NO in mammals is catalyzed solely by three highly regulated isozymes of NOS (Alderton et al., *Biochem J.* 357: 593–615 (2001); Pfeiffer et al., *Angew. Chem. Int. Ed.* 38:1714–1731 (1999); and Stuehr, *Biochim. Biophys. Acta* 1411:217–230 (1999)). In particular, NOSs produce NO from oxidation of L-arginine to L-citrulline via the intermediate N-hydroxy-L-Arg (NHA) (Alderton et al., *Biochem J.* 357:593–615 (2001); Pfeiffer et al., *Angew. Chem. Int. Ed.* 38:1714–1731 (1999); and Stuehr, *Biochim. Biophys. Acta* 1411:217–230 (1999)). Mammalian NOSs are homodimers that contain an N-terminal heme oxygenase domain ($NOS_{oxy}$) and a C-terminal flavoprotein reductase domain ($NOS_{red}$). The oxygenase domain binds L-Arg, heme and the redox-active cofactor 6R-tetrahydrobiopterin ($H_4B$), whereas the reductase domain binds FAD, FMN and NADPH. A calmodulin (CaM) binding sequence links the oxygenase and the reductase domains and regulates reduction of $NOS_{oxy}$ by $NOS_{red}$ in those isoforms that respond to $Ca^{2+}$.

Genome sequencing has revealed truncated NOS proteins in some Gram-positive bacteria, including *Deinococcus radiodurans, Staphylococcus aureus, Bacillus subtilis, B. halodurans* and *B. anthracis*. In general, bacterial NOSs are homologous to the mammalian $NOS_{oxy}$, but lack an associated $NOS_{red}$ and N-terminal regions that bind $Zn^{2+}$, the dihydroxypropyl side chain of $H_4B$, and the adjacent subunit of the dimmer (Pant et al., *Biochemistry* 41:11071–11079 (2002) and Adak et al., *J. Biol. Chem.* 277:16167–16171 (2002)). Nevertheless, the *D. radiodurans* NOS (deiNOS) and *B. subtilis* NOS (bsNOS) are dimeric, have a heme liganded by cysteine thiol, bind substrate L-Arg, and produce nitrogen oxide species in a manner dependent on pterin (either with $H_4B$ or with the related cofactor tetrahydrofolate (THF) (Adak et al., *Proc. Natl. Acad. Sci.* 99:107–12 (2002); Pant et al., *Biochemistry* 41:11071–11079 (2002); and Adak et al., *J. Biol. Chem.* 277:16167–16171 (2002)). The crystal structure of *B. subtilis* NOS, complexed with L-Arg, confirmed that bacterial NOS proteins are similar to mammalian NOSs and NO production has been demonstrated when a mammalian reductase domain is supplied (Adak et al., *J. Biol. Chem.* 277:16167–16171 (2002)). The redox mechanism by which the pterins $H_4B$ and analog THF support NO synthesis in bacterial NOSs mirrors that of the mammalian enzymes (Adak et al., *J. Biol. Chem.* 277:16167–16171 (2002)). A reductase protein that supplies electrons for bacterial NOS catalysis has not yet been identified, although comparisons of bacterial and mammalian NOS structures suggest a common mode of interaction for such a redox partner (Adak et al., *J. Biol. Chem.* 277:16167–16171 (2002)).

Nitrated and nitrosylated natural products, although relatively rare, represent important herbicides, antibiotics, nematicides, fungicides, insecticides, and anti-cancer agents. Nitrated compounds are also key components of explosives, propellants. Despite the importance of nitration and nitrosylation processes for the chemical industry, conventional nitration reactions have drawbacks that include low specificity, low yields, difficult temperature control, difficult product workups, and the generation of waste acids (Pagoria et al., *Thermochim. Acta* 384:187–204 (2002); and Agrawal, *Prog. Energy Combust. Sci.* 24:1–30(1998)). For pyrotechnics, elevated reaction temperatures limit production of unstable products. Regarding pharmaceuticals, greater control of reaction selectivity is desired (Eaton et al., *J. Med. Chem.* 16:290–291(1973); and Hazra et al., *Org. Prep. Proced. Int.* 31:315–319 (1999)). Although nitrated and nitrosylated compounds have vast importance in the pharmaceutical and high-energy materials industries, the chemical processes responsible for the nitration and nitrosylation processes have liabilities in efficacy, cost, and environmental impact. Thus, there is a need for alternative enzymes and methods for conducting nitration/nitrosylation reactions.

The present invention is directed to overcoming these and other deficiencies in the art.

SUMMARY OF THE INVENTION

The present invention relates to an isolated nucleic acid molecule encoding a nitric oxide synthase. The isolated nucleic acid molecule can (i) include a nucleotide sequence of SEQ ID NO:1, SEQ ID NO:3, and/or SEQ ID NO:5; (ii) include a nucleotide sequence that hybridizes to SEQ ID NO:1, SEQ ID NO:3, or SEQ ID NO:5 under stringent conditions characterized by a hybridization medium comprising about 5×SSC at a temperature of about 55° C.; (iii) include a nucleotide sequence having greater than 95 percent homology to a nucleic acid according to SEQ ID NO:1, SEQ ID NO:3, or SEQ ID NO:5; (iv) include a nucleotide sequence that encodes a nitric oxide synthase protein having an amino acid sequence that is at least 85 percent similar to either SEQ ID NO:2, SEQ ID NO:4, or SEQ ID NO:6 by basic BLAST using default parameters analysis; (v) encode a nitric oxide synthase comprising a protein or polypeptide having an amino acid sequence of SEQ ID NO:2, SEQ ID NO:4, and/or SEQ ID NO:6; (vi) encode a nitric oxide synthase comprising a protein or polypeptide having an amino acid motif of SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, and/or combinations thereof; or (vii) encode a nitric oxide synthase protein or polypeptide having an amino acid sequence of SEQ ID NO:47. Expression vectors (e.g., expression systems) and host cells which include the nucleic acid molecules of the present invention are also disclosed. Isolated NOS proteins or polypeptides encoded by the isolated nucleic acid molecules of the present invention are also disclosed. The present invention also relates to a method of recombinantly producing in a host cell the nitric oxide synthases encoded by the nucleic acid molecules of the present invention.

The present invention also relates to a method of attaching a nitrogen group to a target moiety of a compound. This method involves providing a nitric oxide synthase and a compound having a target moiety. The nitric oxide synthase and the compound are combined in a reaction mixture under conditions effective to allow the nitric oxide synthase to catalyze a reaction whereby a nitrogen group contained in the reaction mixture is attached to the target moiety. The method thereby yields a nitrogen-modified compound. Suitable nitric oxide synthases for use in this method can include: (i) a protein or polypeptide having an amino acid sequence that is at least 85 percent similar to either SEQ ID NO:2, SEQ ID NO:4, or SEQ ID NO:6 by basic BLAST using default parameters analysis; (ii) a protein or polypeptide having an amino acid sequence selected from the group consisting of SEQ ID NO:2, SEQ ID NO:4, and SEQ ID NO:6; (iii) a protein or polypeptide having an amino acid motif such as the motif of SEQ ID NO:7, the motif of SEQ ID NO:8, the motif of SEQ ID NO:9, the motif of SEQ ID NO:10, the motif of SEQ ID NO:11, the motif of SEQ ID NO:12, the motif of SEQ ID NO:13, the motif of SEQ ID NO:14, the motif of SEQ ID NO:15, the motif of SEQ ID NO:16, the motif of SEQ ID NO:17, the motif of SEQ ID NO:18, the motif of SEQ ID NO:19, the motif of SEQ ID NO:20, the motif of SEQ ID NO:21, the motif of SEQ ID NO:22, the motif of SEQ ID NO:23, the motif of SEQ ID NO:24, the motif of SEQ ID NO:25, the motif of SEQ ID NO:26, the motif of SEQ ID NO:27, the motif of SEQ ID NO:28, the motif of SEQ ID NO:29, the motif of SEQ ID NO:30, the motif of SEQ ID NO:31, the motif of SEQ ID NO:32, the motif of SEQ ID NO:33, the motif of SEQ ID NO:34, the motif of SEQ ID NO:35, the motif of SEQ ID NO:36, the motif of SEQ ID NO:37, the motif of SEQ ID NO:38, the motif of SEQ ID NO:39, the motif of SEQ ID NO:40, the motif of SEQ ID NO:41, the motif of SEQ ID NO:42, the motif of SEQ ID NO:43, the motif of SEQ ID NO:44, the motif of SEQ ID NO:45, the motif of SEQ ID NO:46, and/or combinations thereof; or (iv) a protein or polypeptide having an amino acid sequence of SEQ ID NO:47, SEQ ID NO:48, SEQ ID NO:49, or SEQ ID NO:50.

The present invention further relates to a method of synthesizing a nitrogen-modified compound in a transgenic host cell. This method involves providing a transgenic host cell transformed with a DNA molecule encoding a nitric oxide synthase. This method also involves providing a non-modified compound containing a target moiety. The transgenic host cell and the non-modified compound are cultured in a culture medium under conditions effective to allow the nitric oxide synthase to be expressed and to catalyze a reaction whereby a nitrogen group contained in the host cell or in a culture medium attaches to the target moiety. The method thereby yields a nitrogen-modified compound. Suitable DNA molecules for use in this method can include those that: (i) have a nucleotide sequence of SEQ ID NO:1, SEQ ID NO:3, and SEQ ID NO:5; (ii) have a nucleotide sequence that hybridizes to SEQ ID NO:1, SEQ ID NO:3, or SEQ ID NO:5 under stringent conditions characterized by a hybridization medium comprising about 5×SSC at a temperature of about 55° C.; (iii) have a nucleotide sequence having greater than 95 percent homology to a nucleic acid according to SEQ ID NO:1, SEQ ID NO:3, or SEQ ID NO:5; (iv) have a nucleotide sequence that encodes a nitric oxide synthase protein having an amino acid sequence that is at least 85 percent similar to either SEQ ID NO:2, SEQ ID NO:4, or SEQ ID NO:6 by basic BLAST using default parameters analysis; (v) encode a nitric oxide synthase having a protein or polypeptide having an amino acid sequence of SEQ ID NO:2, SEQ ID NO:4, and SEQ ID NO:6; (vi) encode a nitric oxide synthase having a protein or polypeptide having amino acid motifs such as the motif of SEQ ID NO:7, the motif of SEQ ID NO:8, the motif of SEQ ID NO:9, the motif of SEQ ID NO:10, the motif of SEQ ID NO:11, the motif of SEQ ID NO:12, the motif of SEQ ID NO:13, the motif of SEQ ID NO:14, the motif of SEQ ID NO:15, the motif of SEQ ID NO:16, the motif of SEQ ID NO:17, the motif of SEQ ID NO:18, the motif of SEQ ID NO:19, the motif of SEQ ID NO:20, the motif of SEQ ID NO:21, the motif of SEQ ID NO:22, the motif of SEQ ID NO:23, the motif of SEQ ID NO:24, the motif of SEQ ID NO:25, the motif of SEQ ID NO:26, the motif of SEQ ID NO:27, the motif of SEQ ID NO:28, the motif of SEQ ID NO:29, the motif of SEQ ID NO:30, the motif of SEQ ID NO:31, the motif of SEQ ID NO:32, the motif of SEQ ID NO:33, the motif of SEQ ID NO:34, the motif of SEQ ID NO:35, the motif of SEQ ID NO:36, the motif of SEQ ID NO:37, the motif of SEQ ID NO:38, the motif of SEQ ID NO:39, the motif of SEQ ID NO:40, the motif of SEQ ID NO:41, the motif of SEQ ID NO:42, the motif of SEQ ID NO:43, the motif of SEQ ID NO:44, the motif of SEQ ID NO:45, the motif of SEQ ID NO:46, and/or combinations thereof; or (vii) encode a nitric oxide synthase having a protein or polypeptide having an amino acid sequence of SEQ ID NO:47, SEQ ID NO:48, SEQ ID NO:49, or SEQ ID NO:50.

The nitric oxide synthases of the present invention are useful for catalyzing specific nitration and/or nitrosylation reactions that can be used in developing more efficient and safe methods of producing nitrated and/or nitrosylated compounds. The present invention could also be useful for bioengineering new bioactive products by incorporation of nitration and nitrosylation events into existing biosynthetic pathways. The nitric oxide synthases of the present invention can also be used to broaden substrate specificity and fine-tune selectivity for the introduction of nitroso and nitro functionalities.

An additional advantage of enzymatically controlled nitration (as provided by the present invention) is the potential for discovering entirely new compounds through bioengineering. For example, genetic incorporation of bacterial NOS into polyketide or non-ribosomal peptide biosynthetic pathways (Kleinkauf et al., *European Journal of Biochemistry* 236:335–351 (1996); and Watanabe et al., *J. Biol Chem.* 278:42020–42026 (2003), which are hereby incorporated by reference in their entirety) will allow generation of novel natural products. Screened with suitable bioassays, nitrated compounds could produce novel leads for drug design.

BRIEF DESCRIPTION OF THE DRAWINGS

FIGS. 1A–1B show the chemical structure of thaxtomin A (FIG. 1A) and the genetic organization of the nos region in the thaxtomin-producing species *Streptomyces turgidiscabies* (FIG. 1B). Thaxtomin A is the predominant thaxtomin congener produced by plant pathogenic *Streptomyces* spp. As shown in FIG. 1B, the txtAB genes of *Streptomyces turgidiscabies* encode two similar peptide synthetases required for synthesis of the dipeptide (Healy et al., *Mol.*

*Micro.* 38:794–804 (2000), which is hereby incorporated by reference in its entirety). The txtC gene encodes a P450 monooxygenase that is required for post-cyclization hydroxylation of the dipeptide. The nos gene is upstream of characterized thaxtomin biosynthetic genes.

Figure 2:
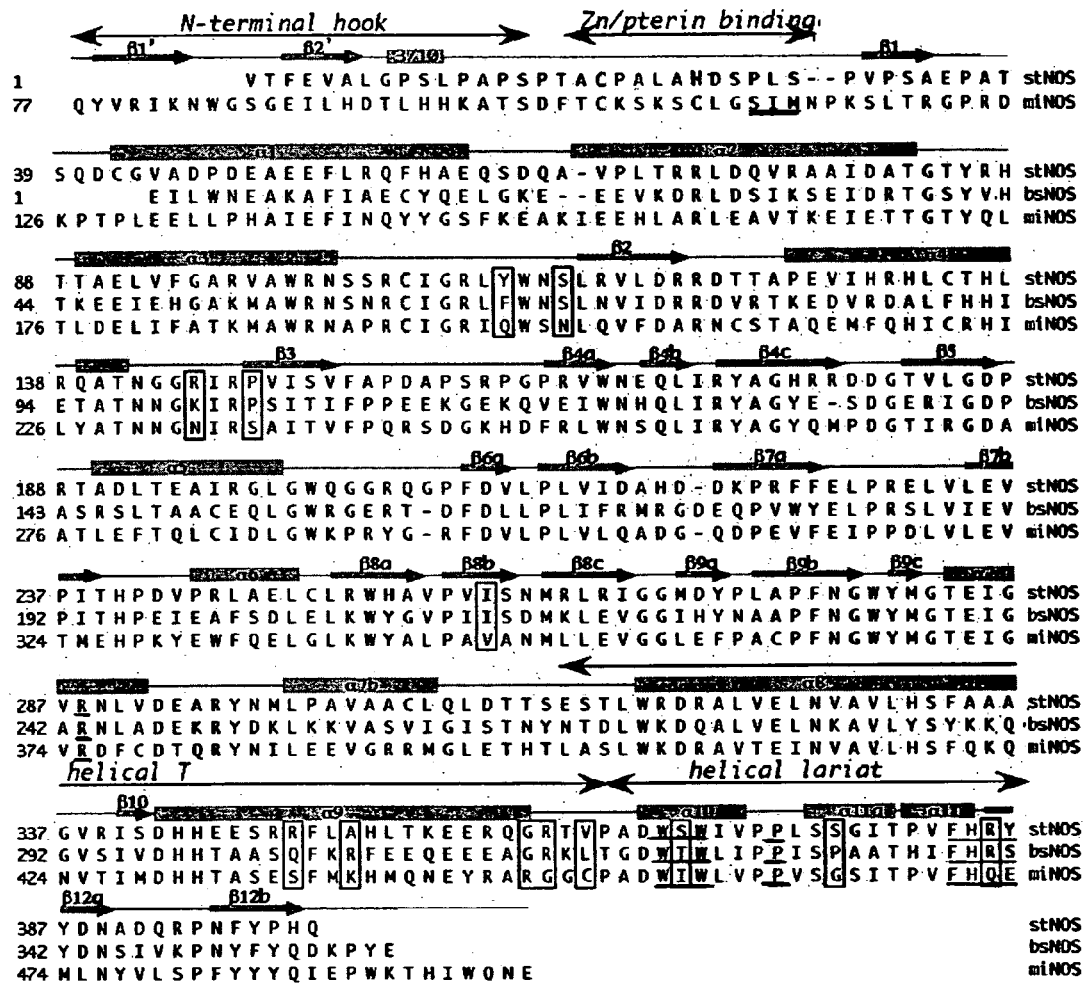

FIG. 2 shows the amino acid sequence alignment of NOSs from *Streptomyces turgidiscabies* (stNOS) (SEQ ID NO:60), *Bacillus subtilis* (bsNOS) (SEQ ID NO:61), and murine iNOS (miNOS) (SEQ ID NO:62). FIG. 2 demonstrates that stNOS is homologous to NOS proteins from *Bacillus subtilis* (bsNOS) and the oxygenase domain of murine iNOS (miNOS). Residues involved in binding substrate L-Arg (bolded letters), pterin cofactor (underlined letters), heme iron and zinc cations (grey letters) are nearly completely conserved among these three classes of $NOS_{oxy}$ proteins. Unlike other bacterial NOSs, stNOS contains an N-terminal extension involved in zinc ion and pterin side-chain binding in miNOS (secondary structure elements and structural motifs for bsNOS shown above in grey, see Pant et al., *Biochemistry* 41:11071–11079 (2002), which is hereby incorporated by reference in its entirety, for nomenclature). The most C-terminal pterin binding residues (stNOS 385 and 386) vary among the proteins because interactions of these residues with pterin are main-chain mediated. Boxed residues indicate positions of different residue character between mammalian and bacterial NOSs. These changes primarily map to the pterin binding site and a site likely involved in reductase protein interactions. The change from Val to Ile at stNOS residue 259 is conserved in all bacterial proteins and increases protection of the immediate distal heme pocket compared to the mammalian proteins.

Figure 3:
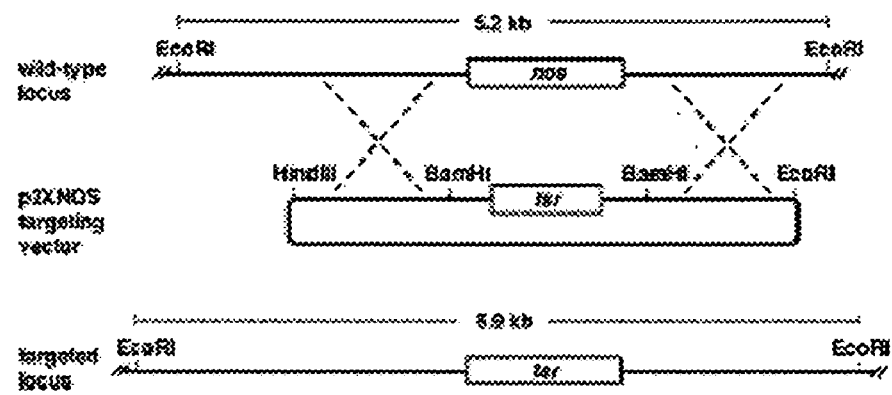
Figure 3:
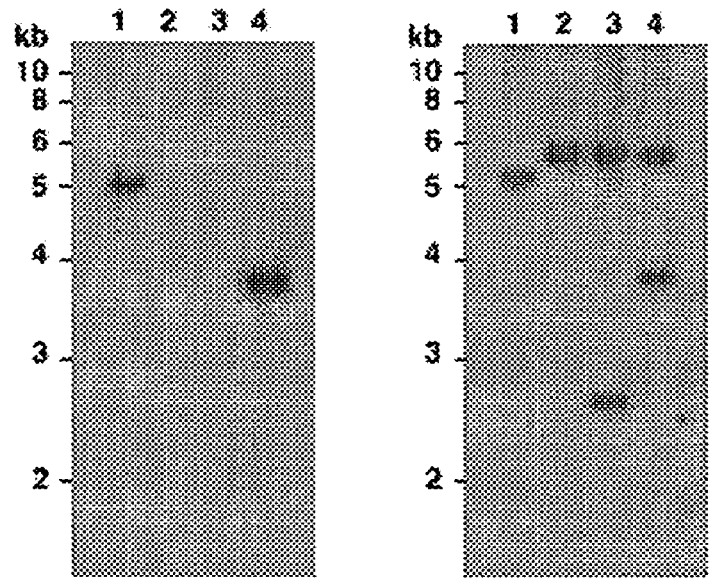
Figure 3:
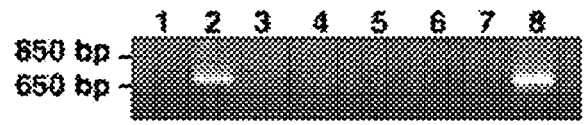

FIGS. 3A–3C show that deletion of nos reduces thaxtomin production by *S. turgidiscabies*. FIG. 3A shows a model for nos replacement in *Streptomyces turgidiscabies* car8 by the p2XNOS targeting vector using marker-exchange mutagenesis. FIG. 3B shows Southern hybridization of an internal 673 bp $^{\alpha\text{-}32}$P labeled nos probe (left) or the $^{\alpha\text{-}32}$P labeled 4.7 kb HindIII/EcoRI p2XNOS insert (right) to EcoRI digests of *S. turgidiscabies* wild-type (lane 1), Δnos (lane 2) Δnos pIJ8600 (empty vector) (lane 3), Δnos pIJ8600NOS (complemented vector)(lane 4) genomic DNA. The thiostrepton resistance gene (tsr) in the p2XNOS insert probe also hybridizes to tsr on pIJ8600 (lanes 3, 4). FIG. 3C shows confirmation of nos expression using RT-PCR. Dnase treated RNA, odd-numbered lanes, cDNA, even-numbered lanes. Wild-type *S. turgidiscabies,* lanes 1, 2; Δnos, lanes 3, 4; Δnos pIJ8600, lanes 5, 6; Δnos pIJ8600NOS, lanes 7, 8.

FIGS. 4A–4C shows that nitrite formation from $N^{\omega}$-hydroxy-L-arginine by recombinant stNOS and sensitivity to inhibitors of mammalian NOSs. FIG. 4A shows *Streptomyces turgidiscabies* NOS Δ41 (residues 41-to carboxy-terminus) cloned into pet28 (Novagene) and expressed in *E. coli* BL-21 cells (lane 3). Full-length stNOS was rapidly degraded in *E. coli,* but the Δ41 construct, which contains all NOS homology regions, produced high levels of protein that were comparable to levels of recombinant *Deinococcus radiodurans* NOS[10] (lane 2) and significantly above levels of background proteins expressed from cells containing the pet28 vector with no NOS insert (lane 1). Sonicated cell lysates from 3 mL cultures were run on 12% SDS-PAGE gels after 2.5 hr induction with 0.1 mM IPTG. Arrow shows the positions of recombinant deiNOS, and stNOS in lanes 2 and 3. FIG. 4B shows nitrite production by cell lysates depicted in FIG. 4A measured by the Griess assay. The NOS intermediate $N^{\omega}$-hydroxy-L-arginine (2 mM) and hydrogen peroxide (4 mM) were reacted with 20 μL of cell lysates shown in FIG. 4A and assayed for nitrite with the Griess reagents after 15 min. Lysates from cells overexpressing stNOS generate nitrite at levels comparable to that of overexpressed deiNOS and significantly above that of the empty vector control (pet28). The selective mammalian NOS inhibitor, nitro-L-arginine (active form of nitro-L-arginine methyl ester), inhibits nitrite formation by lysates expressing stNOS when added to a concentration of 1 mM (same reaction conditions as above). FIG. 4C shows the L-arginine based NOS inhibitors nitro-L-arginine methyl ester (NAME) (32 μM), aminoguanidine (AG) (270 μM), NG-monomethyl-L-arginine (NMMA) (510 μM), and 7-nitroindazole (7-IN) (1.2 μM) each inhibit toxin product without affecting bacterial growth (Standard error reported, n=6).

FIGS. 5A–5B shows that the nitrate nitrogen derives from the guanidine nitrogen of L-Arg. Nuclear magnetic resonance analysis of thaxtomin A extracted from cultures fed either (FIG. 5A) L-Arginine-guanido-$^{15}N_2$.HCl (Cambridge Isotope Laboratories), or (FIG. 5B) $^{15}NH_4NO_3$ (Aldrich). Based on literature values for $^{15}$N atoms in electronic environments similar to those of the four nitrogen atoms in thaxtomin A (Patel et al., *Biochemica. Biophys. Acta.* 1411: 385–400 (1999), which is hereby incorporated by reference in its entirety), the two most upfield peaks at 125 and 114.6 ppm can be assigned to the N-methyls, the broad peak at 132.3 ppm can be assigned to the indole nitrogen, and the downfield peak at 374.8 ppm is diagnostic for the $NO_2$-nitrogen. Accordingly, the single peak (see FIG. 5A) in the spectrum of the L-Arg-guanidino-$^{15}N_2$.HCl supplied sample, at 375.0 ppm represents the signal of the $NO_2$-nitrogen alone.

FIGS. 6A–6B show alignments of the amino acid sequences of the nitric oxide synthases from the following organisms (with the ATCC Accession Numbers representing the GenBank for the nos sequences): *Bacillus anthracis* (ATCC Accession No. AAP29327); *Bacillus cereus* (ATCC Accession No. AAP12306); *Bacillus subtilis* (ATCC Accession No. CAB12592); *Bacillus halodurans* (ATCC Accession No. BAB04542); *Staphylococcus aureus* (ATCC Accession No. BAB95720); *Staphylococcus epidermidis* (ATCC Accession No. AE016749); *Deinococcus radiodurans* (ATCC Accession No. AE002088); *Mus musculus* (ATCC Accession No. AAC52356); *Streptomyces acidiscabies* (ATCC Accession No. AY204508); *Streptomyces scabies* (ATCC Accession No. AY204507); *Streptomyces turgidiscabies* (ATCC Accession No. AY204509); and *Streptomyces avermitilis* (ATCC Accession No. BAC69241).

DETAILED DESCRIPTION OF THE INVENTION

The present invention relates to isolated nucleic acid molecules encoding nitric oxide synthases ("NOSs"). The nitric oxide synthases of the present invention share a common function, in that they function as catalysts for nitration and/or nitrosylation reactions. Also disclosed are expression systems and host cells containing such nucleic acid molecules, as well as isolated proteins or polypeptides encoded by the nucleic acid molecules. Uses of the nucleic acid molecules and the proteins or polypeptides encoded by the nucleic acid molecules are disclosed.

The isolated nucleic acid molecules and their encoded proteins or polypeptides can be, without limitation, from various *Streptomyces* species. Suitable *Streptomyces* species include, for example, *Streptomyces acidiscabies, Streptomyces scabies, Streptomyces turgidiscabies, Streptomyces avermitilis,* and *Streptomyces ipomoea.*

A first isolated nucleic acid molecule of the present invention encodes a nitric oxide synthase ("NOS") from *Streptomyces acidiscabies* (see GenBank Accession No. AY204508) and has a nucleotide sequence according to SEQ ID NO:1 as follows:

```
gtgacctccgaagtcgctctgggcccttccttgcccgccccgtcccgacagcgtgcccggcactg
gggcccgattcgtcccttggcccggtcccgtcggcggaaccggcgacgccgcagtcctgcggcgtc
gccgatccaaatgaggctgaggagttcctgcgccagttccacgcggagcagtccgatcagcccgtc
ccgctcgcccggcgcctggagcaggtccgcgccgccatcgacgccacgggcacctaccggcacacc
accgccgagctcgtgtacggtgcccgcgtcgcgtggcgcaactccagtcgctgcatcggccgcctg
tactggaacagcctgcgcgtcctggaccgccgggacgccacagcccccgatgagatccaccggcac
ttgtgcacgcacctgcgccaggcgaccaacggcgggcgcatcaggccggtgatttcggtcttcgcc
ccggactcccccggccggcccggcccgcaggtgtggaacgagcagctcatccggtacgccggctac
cgccgcgacgacggcaccgtgctcggtgacccgcgcaccgccgacctcaccgaggccatcctccgc
ctcggctggcagggctgccccaagggccgttcgacgtcctgcccctggtcatcgacaccccgac
gacaaacccggttcttcgagctgccgcgggagctggtcttggaggtccctatcacccaccccgac
gtcccacgcctggccgaactgggcctgcgctggcacgccgtaccgtcatctccaacatgcgccta
cgcatcggcgggatggactaccgctcgccccgttcaacggctggtacatgggcacggagatcggc
gcccgcaacctcgtcgacgaggaccgctacaacatgctccccgccgtcgccgcctgcctccagctg
gacaccaccagcgagtcaaccctgtggcgcgaccgcgccctggtcgagctcaacgtcgccgtcctg
cactccttcgaggccgcaggtgtccggatcagcgaccaccacgaggagtcccggcgcttcctcgcc
cacctggccaaggaggaacgccagggccgcaccgtatccgcagactggagctggatcgtcccccg
ctctccggcggcatcaccccgtgttccaccgttactacgacaacgtcgaccagcgccccaacttc
taccccaccagtga
```

The NOS protein or polypeptide encoded by this nucleic acid molecule has an amino acid sequence according to SEQ ID NO:2 as follows:

```
MTSEVALGPSLPAPSPTACPALGPDSSLGPVPSAEPATPQSCGVADPNEAEEFLRQFHAEQSDQPV
PLARRLEQVRAAIDATGTYRHTTAELVYGARVAWRNSSRCIGRLYWNSLRVLDRRDATAPDEIHRH
LCTHLRQATNGGRIRPVISVFAPDSPGRPGPQVWNEQLIRYAGYRRDDGTVLGDPRTADLTEAILR
LGWQGCPQGPFDVLPLVIDTPDDKPRFFELPRELVLEVPITHPDVPRLAELGLRWHAVPVISNMRL
RIGGMDYPLAPFNGWYMGTEIGARNLVDEDRYNMLPAVAACLQLDTTSESTLWRDRALVELNVAVL
HSFEAAGVRISDHHEESRRFLAHLAKEERQGRTVSADWSWIVPPLSGGITPVFHRYYDNVDQRPNF
YPHQ
```

A second isolated nucleic acid molecule of the present invention encodes a NOS from *Streptomyces scabies* (see GenBank Accession No. AY204507) and has a nucleotide sequence according to SEQ ID NO:3 as follows:

```
gtgacctccgaagtcgctctgggcccttccttgcccgccccgtcccgacagcgtgcccggcactg
gggcccgattcgtcccttggcccggtcccgtcggcggaaccggcgacgccgcagtcctgcggcgtc
gccgatccaaatgaggctgaggagttcctgcgccagttccacgcggagcagtccgatcagcccgtc
ccgctcgcccggcgcctggagcaggtccgcgccgccatcgacgccacgggcacctaccggcacacc
accgccgagctcgtgtacggtgcccgcgtcgcgtggcgcaactccagtcgctgcatcggccgcctg
tactggaacagcctgcgcgtcctggaccgccgggacgccacagcccccgatgagatccaccggcac
ttgtgcacgcacctgcgccaggcgaccaacggcgggcgcatcaggccggtgatttcggtcttcgcc
```

-continued

```
ccggactccccggccggcccggcccgcaggtgtggaacgagcagctcatccggtacgccggctac cgccgcgacgacggcaccgtgctcggtgaccgcgcaccgccgacctcaccgaggccatcctccgc ctcggctggcagggctgccccaagggccgttcgacgtcctgccctggtcatcgacaccccgac gacaaacccggttcttcgagctgccgcgggagctggtcttggaggtccctatcacccaccccgac gtcccacgcctggccgaactgggcctgcgctggcacgccgtacccgtcatctccaacatgcgccta cgcatcggcgggatggactaccgctcgcccgttcaacggctggtacatgggcacggagatcggc gcccgcaacctcgtcgacgaggaccgctacaacatgctccccgccgtcgccgctgcctccagytg gacaccaccagcgagtcaaccctgtggcgcgaccgcgccctggtcgagctcaacgtcgccgtcctg cactccttcgaggccgcaggtgtccggatcagcgaccaccacgaggagtcccggcgcttcctcgcc cacctggccaaggaggaacgccagggccgcaccgtatccgcagactggagctggatcgtcccccg ctctccggcggcatcaccccgtgttccaccgttactacgacaacgtcgaccagcgccccaacttc taccccaccagtga
```

The NOS protein or polypeptide encoded by this nucleic acid molecule has an amino acid sequence according to SEQ ID NO:4 as follows:

```
MTSEVALGPSLPAPSPTACPALGPDSSLGPVPSAEPATPQSCGVADPNEAEEFLRQFHAEQSDQPV

PLARRLEQVRAAIDATGTYRHTTAELVYGARVAWRNSSRCIGRLYWNSLRVLDRRDATAPDEIHRH

LCTHLRQATNGGRIRPVISVFAPDSPGRPGPQVWNEQLIRYAGYRRDDGTVLGDPRTADLTEAILR

LGWQGCPQGPFDVLPLVIDTPDDKPRFFELPRELVLEVPITHPDVPRLAELGLRWHAVPVISNMRL

RIGGMDYPLAPFNGWYMGTEIGARNLVDEDRYNMLPAVAACLQLDTTSESTLWRDRALVELNVAVL

HSFEAAGVRISDHHEESRRFLAHLAKEERQGRTVSADWSWIVPPLSGGITPVFHRYYDNVDQRPNF

YPHQ
```

A third isolated nucleic acid molecule of the present invention encodes a from *Streptomyces turgidiscabies* (see GenBank Accession No. AY204509) and has a nucleotide sequence according to SEQ ID NO:5 as follows:

```
gtgactttcgaagtcgccctgggccttccttgcccgccccgtccccgacagcgtgcccggcgctg gcgcacgattcgcccctcagtcccgtcccgtcggcggaaccggcgacgtcgcaggactgcggcgtc gccgatccagacgaggccgaggagttcctgcgccagtttcacgcggagcagtccgaccaggccgtc ccgctcactcggcgcctggaccaggttcgcgctgccatcgacgccacgggcacctaccgtcatacc accgccgagctcgtgttcggtgcccgtgtcgcgtggcgcaactccagtcgctgtatcggccgcctg tactggaacagcctgcgcgtcctggaccgccgggacaccacagccccgaggtaatccaccggcac ctttgcacgcacctgcgccaggcgaccaacggtgggcgtatcaggccggtgatttcggtcttcgcc ccggacgcacccagccgacccggcccgcgggtgtggaacgagcaactcgtccggtacgccggccac cgtcgcgacgacggcaccgtactcggcgacccgcgatctgccgacctcaccgaggccatccgcggc ctcggatggcaggagccgccaagggccgttcgacgtcctgccctggtcatcgacgccacgac gacaaaccgcggttcttcgagctgccgcgggaggttgtcctggaggtccctatcacccaccccgac gtcccacgactggccgaactctgcctgcgctggcacgccgtacccgttatctccaacatgcgcctg cgtatcggcggggtggactacccctcgccccgttcaacggctggtacatgggcacggagatcggc
```

```
                                    -continued
gtccgtaacctcgtcgacgaggcccgctacaacctgctccccgccgtggccgcctgcctccagttg gacaccaccagcgagtccaccctgtggcgtgaccgcgctctggtcgaactcaacgttgccgtcttg cactctttcgcggccgcaggcgtccggatcagtgaccaccacgaggagtcccggcgcttcctcgcc cacctgaccaaggaggaacgccagggccgcaccgtacccgcggactggagctggatcgtccctccg ctttccagcggcatcaccccgtcttccaccgctactacgacaacgccgaccagcgccccaactttt taccctcatcagtga
```

The NOS protein or polypeptide encoded by this nucleic acid molecule has an amino acid sequence according to SEQ ID NO:6 as follows:

```
MTFEVALGPSLPAPSPTACPALAHDSPLSPVPSAEPATSQDCGVADPDEAEEFLRQFHAEQSDQAV

PLTRRLDQVRAAIDATGTYRHTTAELVFGARVAWRNSSRCIGRLYWNSLRVLDRRDTTAPEVIHRH

LCTHLRQATNGGRIRPVISVFAPDAPSRPGPRVWNEQLVRYAGHRRDDGTVLGDPRSADLTEAIRG

LGWQGGRQGPFDVLPLVIDAHDDKPRFFELPREVVLEVPITHPDVPRLAELCLRWHAVPVISNMRL

RIGGVDYPLAPFNGWYMGTEIGVRNLVDEARYNLLPAVAACLQLDTTSESTLWRDRALVELNVAVL

HSFAAAGVRISDHHEESRRFLAHLTKEERQGRTVPADWSWIVPPLSSGITPVFHRYYDNADQRPNF

YPHQ
```

Fragments of the above-identified proteins or polypeptides as well as fragments of full length proteins can also be used according to the present invention.

Suitable fragments can be produced by several means. Subclones of the gene encoding a known protein can be produced using conventional molecular genetic manipulation for subcloning gene fragments, such as described by Sambrook et al., *Molecular Cloning: A Laboratory Manual*, Cold Springs Laboratory, Cold Springs Harbor, N.Y. (1989), and Ausubel et al. (ed.), *Current Protocols in Molecular Biology*, John Wiley & Sons (New York, N.Y.) (1999 and preceding editions), each of which is hereby incorporated by reference in its entirety. The subclones then are expressed in vitro or in vivo in bacterial cells to yield a smaller protein or polypeptide that can be tested for activity. Various other cloning protocols known in the art are suitable for use in the present invention, including, for example, those described for *Streptomyces* in Hopwood et al., *Genetic manipulation of Streptomyces: A Laboratory Manual*, Norwich: John Innes Foundation (1985) and Kieser et al., *Practical Streptomyces Genetics* Norwich: John Innes Foundation (2000), which are hereby incorporated by reference in their entirety.

In another approach, based on knowledge of the primary structure of the protein, fragments of the protein-coding gene may be synthesized using the PCR technique together with specific sets of primers chosen to represent particular portions of the protein. Erlich, H. A., et al., "Recent Advances in the Polymerase Chain Reaction," *Science* 252: 1643–51 (1991), which is hereby incorporated by reference. These can then be cloned into an appropriate vector for expression of a truncated protein or polypeptide from bacterial cells as described above.

As an alternative, fragments of a protein can be produced by digestion of a full-length protein with proteolytic enzymes like chymotrypsin or *Staphylococcus* proteinase A, or trypsin. Different proteolytic enzymes are likely to cleave different proteins at different sites based on the amino acid sequence of the particular protein. Some of the fragments that result from proteolysis may be active virulence proteins or polypeptides.

Chemical synthesis can also be used to make suitable fragments. Such a synthesis is carried out using known amino acid sequences for the polypeptide being produced. Alternatively, subjecting a full length protein to high temperatures and pressures will produce fragments. These fragments can then be separated by conventional procedures (e.g., chromatography, SDS-PAGE).

Another example of suitable fragments of the nucleic acids of the present invention are fragments of the genes which have been identified as conserved ("con") regions of the proteins, or alternatively, those portions of nucleotide sequences that have been identified as variable ("var") regions. Conserved regions in accordance with the present invention are further described infra. Sequences identified using DNAStar Mega alignment program as either variable or conserved in a gene can be amplified using standard PCR methods using forward and reverse primers designed to amplify the region of choice and which include a restriction enzyme sequence to allow ligation of the PCR product into a vector of choice. Combinations of amplified conserved and variable region sequences can be ligated into a single vector to create a "cassette" which contains a plurality of DNA molecules in one vector.

Also suitable as an isolated nucleic acid molecule according to the present invention is a nucleic molecule having a nucleotide sequence that encodes a NOS protein or polypeptide having an amino acid motif that is a conserved region of the NOS protein or polypeptide from *Streptomyces acidiscabies, Streptomyces scabies,* and *Streptomyces turgidiscabies* (as described in Table 1, below).

TABLE 1

Conserved Regions of the NOS Proteins or Polypeptides From *Streptomyces acidiscabies*, *Streptomyces scabies*, and *Streptomyces turgidiscabies*

| Location[1] | Motif | |
|---|---|---|
| 4–22 | EVALGPSLPAPSPTACPAL | (SEQ ID NO: 7) |
| 30–38 | PVPSAEPAT | (SEQ ID NO: 8) |
| 42–47 | CGVADP | (SEQ ID NO: 9) |
| 49–64 | EAEEFLRQFHAEQSDQ | (SEQ ID NO: 10) |
| 74–93 | QVRAAIDATGTYRHTTAELV | (SEQ ID NO: 11) |
| 95–122 | GARVAWRNSSRCIGRLYWNSLRVLDRRD | (SEQ ID NO: 12) |
| 129–156 | IHRHLCTHLRQATNGGRIRPVISVFAPD | (SEQ ID NO: 13) |
| 165–170 | VWNEQL | (SEQ ID NO: 14) |
| 177–188 | RRDDGTVLGDPR | (SEQ ID NO: 15) |
| 190–196 | ADLTEAI | (SEQ ID NO: 16) |
| 199–203 | LGWQG | (SEQ ID NO: 17) |
| 206–217 | QGPFDVLPLVID | (SEQ ID NO: 18) |
| 220–231 | DDKPRFFELPRE | (SEQ ID NO: 19) |
| 233–249 | VLEVPITHPDVPRLAEL | (SEQ ID NO: 20) |
| 251–268 | LRWHAVPVISNMRLRIGG | (SEQ ID NO: 21) |
| 270–286 | DYPLAPFNGWYMGTEIG | (SEQ ID NO: 22) |
| 288–293 | RNLVDE | (SEQ ID NO: 23) |
| 299–333 | LPAVAACLQLDTTSESTLWRDRALVELNVAVLHSF | (SEQ ID NO: 24) |
| 335–354 | AAGVRISDHHEESRRFLAHL | (SEQ ID NO: 25) |
| 356–364 | KEERQGRTV | (SEQ ID NO: 26) |
| 366–389 | ADWSWIVPPLSGGITPVFHRYYDN | (SEQ ID NO: 27) |
| 391–400 | DQRPNFYPHQ | (SEQ ID NO: 28) |

[1]The "Location" refers to the range of amino acid residues as corresponding to the amino acid sequence of the NOS from *Streptomyces acidiscabies* (i.e., SEQ ID NO: 2).

Thus, one aspect of the present invention includes an isolated nucleic acid molecule that encode a NOS protein or polypeptide having an amino acid motif having an amino acid sequence of one of the following: SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22; SEQ ID NO:23; SEQ ID NO:24; SEQ ID NO:25; SEQ ID NO:26; SEQ ID NO:27; SEQ ID NO:28; and/or combinations thereof.

The information presented in Table 1 can be combined to define a NOS protein or polypeptide of the present invention as having an amino acid sequence of SEQ ID NO:47 (with X being any amino acid) as follows:

(3X–49X) EVALGPSLPAPSPTACPAL (7X) PVPSAEPAT (3X)

CGVADP (1X) EAEEFLRQFHAE QSDQ (9X)

QVRAAIDATGTYRHTTAELV (1X)

GARVAWRNSSRCIGRLYWNSLRVLDRRD (6X) IH

RHLCTHLRQATNGGRIRPVISVFAPD (8X) VWNEQL (6X)

RRDDGTVLGDPR (1X) ADLTEAI (2X) LGWQG (2X)

QGPFDVLPLVID (2X) DDKPRFFELPRE (1X)

VLEVPITHPDVPRLAEL (1X) LRWHAVPVISNMRLRIGG (1X)

DYPLAPFNGWYMGTEIG (1X) RNLVDE (5X) LPAVAACLQLDTT

SESTLWRDRALVELNVAVLHSF (1X) AAGVRISDHHEESRRFLAHL (1X) KEERQGRTV (1X) ADW SWIVPPLSGGITPVFHRYYDN (1X)

DQRPNFYPHQ

Mutations or variants of the above polypeptides or proteins are encompassed by the present invention. Variants may be made by, for example, the deletion or addition of amino acids that have minimal influence on the properties, secondary structure, and hydropathic nature of a polypeptide or protein. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification, or identification of the polypeptide.

Also suitable as an isolated nucleic acid molecule according to the present invention is a nucleic acid molecule having a nucleotide sequence that is at least 55 percent similar, particularly at least 85 percent similar, and more particularly at least 90 percent similar to the nucleotide sequence of SEQ ID NO:1, SEQ ID NO:3, or SEQ ID NO:5 by basic BLAST using default parameters analysis. Another suitable isolated nucleic acid of the present invention is one having a nucleotide sequence having at least 60 percent homology, particularly at least 70 percent homology, more particularly at least 80 percent homology, more particularly at least 90 percent homology, and still more particularly at least 95 percent homology to a nucleic acid according to SEQ ID NO:1, SEQ ID NO:3, or SEQ ID NO:5.

Suitable nucleic acid molecules also include those that hybridize to a nucleic acid molecule comprising a nucleotide sequence of SEQ ID NO:1, SEQ ID NO:3, or SEQ ID NO:5 under stringent conditions. For the purposes of defining the level of stringency, reference can conveniently be made to Sambrook et al., *Molecular Cloning: a Laboratory Manual*, $2^{nd}$ Edition, Cold Spring Harbor, N.Y., Cold Spring Harbor Laboratory Press, at 11.45 (1989), which is hereby incorporated by reference in its entirety). An example of low stringency conditions is 4–6×sodium citrate ("SSC")/ 0.1–0.5% w/v SDS at 37°–45° C. for 2–3 hours. Depending on the source and concentration of the nucleic acid involved in the hybridization, alternative conditions of stringency may be employed such as medium stringent conditions. Examples of medium stringent conditions include 1–4×SSC/ 0.25% w/v SDS at ≧45° C. for 2–3 hours. An example of high stringency conditions includes 0.1–1×SSC/0.1% w/v SDS at 60° C. for 1–3 hours. The skilled artisan is aware of various parameters which may be altered during hybridization and washing and which will either maintain or change the stringency conditions. Other examples of high stringency conditions include: 4–5×SSC/0.1% w/v SDS at 54° C. for 1–3 hours and 4×SSC at 65° C., followed by a washing in 0.1×SSC at 65° C. for about one hour. Alternatively, an exemplary stringent hybridization condition is in 50% formamide, 4×SSC, at 42° C. Still another example of stringent conditions include hybridization at 62° C. in 6×SSC, 0.05× BLOTTO, and washing at 2×SSC, 0.1% SDS at 62° C. In one particular embodiment, the stringent conditions are characterized by a hybridization medium including about 5×SSC at a temperature of about 55° C.

The precise conditions for any particular hybridization are left to those skilled in the art because there are variables involved in nucleic acid hybridizations beyond those of the specific nucleic acid molecules to be hybridized that affect the choice of hybridization conditions. These variables include: the substrate used for nucleic acid hybridization (e.g., charged vs. non-charged membrane); the detection method used (e.g., radioactive vs. chemiluminescent); and the source and concentration of the nucleic acid involved in the hybridization. All of these variables are routinely taken into account by those skilled in the art prior to undertaking a nucleic acid hybridization procedure.

A nitric oxide synthase protein or polypeptide of the present invention is preferably produced in purified form (e.g., at least about 80 percent, more preferably 90 percent pure) by conventional techniques. For example, a nitric oxide synthase protein or polypeptide of the present invention may be secreted into the growth medium of recombinant host cells. To isolate the nitric oxide synthase protein or polypeptide, a protocol involving a host cell such as *Escherichia coli* may be used, in which protocol the *E. coli* host cell carrying a recombinant plasmid is propagated, homogenized, and the homogenate is centrifuged to remove bacterial debris. The supernatant is then subjected to sequential ammonium sulfate precipitation. The fraction containing the nitric oxide synthase protein or polypeptide of the present invention is subjected to gel filtration in an appropriately sized dextran or polyacrylamide column to separate the proteins or polypeptides. If necessary, the protein fraction may be further purified by high performance liquid chromatography ("HPLC").

The present invention relates to a DNA construct that contains a DNA molecule encoding for a nitric oxide synthase protein or polypeptide of the present invention. This involves incorporating one or more of the nucleic acid molecules of the present invention, or a suitable portion thereof, into host cells using conventional recombinant DNA technology. Generally, this involves inserting the nucleic acid molecule into an expression system to which the nucleic acid molecule is heterologous (i.e., not normally present). The expression system contains the necessary elements for the transcription and translation of the inserted protein-coding sequences.

The present invention also relates to an expression system (e.g., an expression vector) containing a nucleic acid molecule encoding a nitric oxide synthase protein or polypeptide of the present invention. The nucleic acid molecules of the present invention may be inserted into any of the many available expression vectors and cell systems using reagents that are well known in the art. In preparing a DNA vector for expression, the various DNA sequences may normally be inserted or substituted into a bacterial plasmid. Any convenient plasmid may be employed, which will be characterized by having a bacterial replication system, a marker which allows for selection in a bacterium, and generally one or more unique, conveniently located restriction sites. Numerous plasmids, referred to as transformation vectors, are available for transformation. The selection of a vector will depend on the preferred transformation technique and target cells for transfection.

Suitable vectors include, but are not limited to, the following viral vectors such as lambda vector system gt11, gt WES.tB, Charon 4, and plasmid vectors such as pBR322, pBR325, pACYC177, pACYC1084, pUC8, pUC9, pUC18, pUC19, pLG339, pR290, pKC37, pKC101, SV 40, pBluescript II SK+/– or KS+/– (see "Stratagene Cloning Systems" Catalog (1993) from Stratagene, La Jolla, Calif., which is hereby incorporated by reference in its entirety), pQE, pIH821, pGEX, pET series (see F. W. Studier et. al., "Use of T7 RNA Polymerase to Direct Expression of Cloned Genes," *Gene Expression Technology*, Vol. 185 (1990), which is hereby incorporated by reference in its entirety), pCB201, and any derivatives thereof. Any appropriate vectors now known or later described for genetic transformation are suitable for use with the present invention. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, Second Edition, Cold Spring Harbor Press, N.Y. (1989), and Ausubel, F. M. et al. (1989) *Current Protocols in Molecular Biology*, John Wiley & Sons, New York, N.Y., which are hereby incorporated by reference in their entirety.

U.S. Pat. No. 4,237,224 issued to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

A variety of host-vector systems may be utilized to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Thus, certain "control elements" or "regulatory sequences" are also incorporated into the plasmid-vector constructs of the present invention. These include non-transcribed regions of the vector and 5' and 3' untranslated regions, which interact with host cellular proteins to carry out transcription and translation. Such elements may vary in their strength and specificity. Depending on the vector system and host utilized, any number of suitable transcription and/or translation elements, including constitutive, inducible, and repressible promoters, as well as minimal 5' promoter elements may be used. A constitutive promoter is a promoter that directs expression of a gene throughout the development and life of an organism. An inducible promoter is a promoter that is capable of directly or indirectly activating transcription of one or more DNA sequences or genes in response to an inducer. In the absence of an inducer, the DNA sequences or genes will not be transcribed or will only be minimally transcribed.

The DNA sequences of eukaryotic promoters differ from those of prokaryotic promoters. Furthermore, eukaryotic promoters and accompanying genetic signals may not be recognized in or may not function in a prokaryotic system, and, further, prokaryotic promoters are not recognized and do not function in eukaryotic cells.

Promoters vary in their "strength" (i.e. their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *E. coli*, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited to, lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Other examples of some constitutive promoters that are widely used for inducing expression of transgenes include the nopoline synthase gene promoter from *Agrobacterium tumefaciens* (U.S. Pat. No. 5,034,322 issued to Rogers et al., which is hereby incorporated by reference in its entirety), the cauliflower mosaic virus (CaMV) 35S and 19S promoters (U.S. Pat. No. 5,352,605 issued to Fraley et al., which is hereby incorporated by reference in its entirety), the enhanced CaMV35S promoter ("enh CaMV35S"), the figwort mosaic virus full-length transcript promoter ("FMV35S"), those derived from any of the several actin genes, which are known to be expressed in most cells types (U.S. Pat. No. 6,002,068 issued to Privalle et al., which is hereby incorporated by reference in its entirety), and the ubiquitin promoter, which is a gene product known to accumulate in many cell types. Examples of constitutive promoters for use in mammalian cells include the RSV promoter derived from Rous sarcoma virus, the CMV promoter derived from cytomegalovirus, β-actin and other actin promoters, and the EF1α promoter derived from the cellular elongation factor 1α gene.

Bacterial host cell strains and expression vectors may be chosen which inhibit the action of the promoter unless specifically induced. In certain operations, the addition of specific inducers is necessary for efficient transcription of the inserted nucleic acid. For example, the lac operon is induced by the addition of lactose or IPTG (isopropylthio-beta-D-galactoside). A variety of other operons, such as trp, pro, etc., are under different controls.

Other examples of some inducible promoters, induced, for examples by a chemical agent, such as a metabolite, growth regulator, herbicide or phenolic compound, or a physiological stress/physical means, such as cold, heat, salt, toxins, or through the action of a pathogen or disease agent such as a virus or fungus, include a glucocorticoid-inducible promoter (Schena et al., *Proc. Natl. Acad. Sci.* 88:10421–5 (1991), which is hereby incorporated by reference in its entirety), the heat shock promoter ("Hsp"), IPTG or tetracycline ("Tet on" system), the metallothionine promoter, which is activated by heavy metal ions, and hormone-responsive promoters, which are activated by treatment of certain hormones. A host cell containing an inducible promoter may be exposed to an inducer by externally applying the inducer to the cell. In addition, "tissue-specific" promoters can be used, which are promoters that function in a tissue specific manner to regulate the gene of interest within selected tissues of the host. Examples of such tissue specific promoters include seed, flower, or root specific promoters as are well known in the field (e.g., U.S. Pat. No. 5,750,385 to Shewmaker et al., which is hereby incorporated by reference in its entirety). Promoters of the nucleic acid construct of the present invention may be either homologous (derived from the same species as the host cell) or heterologous (derived from a different species than the host cell).

Specific initiation signals are also required for efficient gene transcription and translation in prokaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in *E. coli* requires an SD sequence about 7–9 bases 5' to the initiation codon ("ATG") to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

The constructs of the present invention also include an operable 3' regulatory region, selected from among those which are capable of providing correct transcription termination and polyadenylation of mRNA for expression in the host cell of choice, operably linked to a DNA molecule which encodes for a protein of choice. A number of 3' regulatory regions are known in the art. Virtually any 3' regulatory region known to be operable in the host cell of choice would suffice for proper expression of the coding sequence of the nucleic acid of the present invention.

In one aspect of the present invention, the nucleic acid molecule of the present invention is incorporated into an appropriate vector in the sense direction, such that the open reading frame is properly oriented for the expression of the encoded protein under control of a promoter of choice. This involves the inclusion of the appropriate regulatory elements into the DNA-vector construct. These include non-translated regions of the vector, useful promoters, and 5' and 3' untranslated regions which interact with host cellular proteins to carry out transcription and translation. Such elements may vary in their strength and specificity. Depending on the vector system and host utilized, any number of suitable transcription and translation elements, including constitutive and inducible promoters, may be used.

A nucleic acid molecule of the preset invention, promoter of choice, an appropriate 3' regulatory region, and, if desired, a reporter gene, can be incorporated into a vector-expression system to contain a nucleic acid of the present invention, or a suitable fragment thereof, using standard cloning techniques as described in Sambrook et al., *Molecular Cloning: A Laboratory Manual,* Second Edition, Cold Spring Harbor Press, NY (1989), and Ausubel et al. (1989) *Current Protocols in Molecular Biology,* John Wiley & Sons, New York, N.Y., which are hereby incorporated by reference in their entirety. The transcriptional and translational elements are operably linked to the nucleic acid molecule of the present invention or a fragment thereof, meaning that the resulting vector expresses the nitric oxide synthase protein or polypeptide when placed in a suitable host cell.

Once an isolated DNA molecule encoding a nitric oxide synthase protein or polypeptide has been cloned into an expression vector, it is ready to be incorporated into a host cell. Such incorporation can be carried out by the various forms of transformation noted above, depending upon the vector/host cell system. Recombinant molecules can be introduced into cells via transformation, particularly transduction, conjugation, mobilization, or electroporation. The nucleic acid sequences are cloned into the host cell using standard cloning procedures known in the art, as described by Sambrook et al., *Molecular Cloning: A Laboratory Manual,* Second Edition, Cold Springs Laboratory, Cold Springs Harbor, N.Y. (1989), which is hereby incorporated by reference in its entirety. Suitable host cells include, but are not limited to, bacteria, virus, yeast, mammalian cells, insect, plant, and the like. Examples of a suitable bacterial host cells include, without limitation, *Streptomyces, Bacillus, Escherichia, Brevibacterium, Microbacterium, Nocardia,* and *Rhodococcus* cells. Particular *Streptomyces* host cells can include *Streptomyces acidiscabies, Streptomyces scabies, Streptomyces turgidiscabies, Streptomyces avermitilis, Streptomyces lividans, Streptomyces coelicolor,* and *Streptomyces ipomoea.* Particular *Escherichia* host cells can include *Escherichia coli.* Particular *Bacillus* host cells can include *Bacillus subtilis, Bacillus anthracis, Bacillus cereus,* and *Bacillus halodurans.* Examples of suitable fungal host cells include, without limitation, *Aspergillus, Cephalosporium,* and *Penicillium* cells. Suitable yeast host cells include, without limitation, *Saccharomyces* cells.

Thus, the present invention also relates to a host cell incorporating one or more of the isolated nucleic acid molecules of the present invention. In one embodiment, the isolated nucleic acid molecule is heterologous to the host cell. Such incorporation can be carried out by the various forms of transformation noted above, depending upon the vector/host system, and using the various host cells described above.

Methods of transformation may result in transient or stable expression of the DNA under control of the promoter. Preferably, the nucleic acid of the present invention is stably inserted into the genome of the host cell as a result of the transformation, although transient expression can serve an important purpose.

The present invention also relates to a method of attaching a nitrogen group to a target moiety of a compound. This method involves providing a nitric oxide synthase. The method also involves providing a compound having a target moiety to which can be attached a nitrogen group. The nitric oxide synthase and the compound are combined in a reaction mixture under conditions effective to allow the nitric oxide synthase to catalyze a reaction whereby a nitrogen group contained in the reaction mixture is attached to the target moiety. The method thereby yields a nitrogen-modified compound.

The present invention further relates to a method of synthesizing a nitrogen-modified compound in a transgenic host cell. This method involves providing a transgenic host cell transformed with a DNA molecule encoding a nitric oxide synthase. A non-modified compound containing a target moiety is also provided. The transgenic host cell and the non-modified compound are cultured in a culture medium under conditions effective to allow the nitric oxide synthase to be expressed and to catalyze a reaction whereby a nitrogen group contained in the host cell or culture medium attaches to the target moiety. The method thereby yields a nitrogen-modified compound. The non-modified compound containing a target moiety can be provided exogenously. Alternatively, the non-modified compound containing a target moiety can be produced by the transgenic host cell. Suitable DNA molecules include those of the present invention, as well as those encoding the various nitric oxide synthases described herein (and as specifically identified infra).

As used herein, the term "Nitrogen-Modifying Methods" refers to the above-referenced "method of attaching a nitrogen group to a target moiety of a compound" and "method of synthesizing a nitrogen-modified compound in a transgenic host cell." Suitable host cells, nitrogen groups, target moieties, and nitrogen-modified compounds for use in the Nitrogen-Modifying Methods of the present invention are further described below.

In one example for conducting the Nitrogen-Modifying Methods of the present invention, the NOS-mediated nitration and/or nitrosylation can proceed by incubating the compound (e.g., molecule) having the target moiety targeted for modification with the following: (i) a nitric oxide synthase of the present invention (which functions as a catalyst for nitration and/or nitrosylation); (ii) a nitrogen-containing substrate for NOS (also referred to herein as the "NOS substrate"); and (iii) a source of oxygen (e.g., reduced oxygen). A suitable NOS substrate can include any nitrogen-containing molecule that can bind at the NOS heme center and be converted to an oxidized form of nitrogen capable of nitration and/or nitrosylation reactions. For example, the NOS substrate can contain either a guanidinum group, an hydroxy-guanidinium group, and/or an oxime group. Oxygen can be supplied in the form of molecular oxygen ($O_2$), reduced oxygen (e.g., peroxide ($O_2^{2-}$) or superoxide ($O_2^-$)), or as an oxo-donor compound such as m-chloroperoxybenzoic acid. Depending on the oxygen and nitrogen-containing substrate used, additional reducing equivalents may be provided in the form of small molecule electron donors (e.g., dithionite, reduced methyl viologen) or as a reductase protein (e.g., iron-sulfur cluster, heme, or flavin-containing enzymes).

Suitable nitric oxide synthases for use in the Nitrogen-Modifying Methods of the present invention can include any nitric oxide synthase (from any source) that can function as a catalyst in a nitration and/or nitrosylation reaction. Examples of such suitable nitric oxide synthases are those described herein and/or encoded by the isolated nucleic acid molecules of the present invention (described supra). Other suitable examples of nitric oxide synthases or nucleic acid molecules for use in the Nitrogen-Modifying Methods include those that have (or encode) the following three conserved amino acid regions (i.e., motifs): (i) the RCIGR (SEQ ID NO:44) motif (corresponding to amino acid residues 105–109 of the nitric oxide synthase of *Streptomyces acidiscabies* (SEQ ID NO:2)), which functions to coordinate the iron of the heme prosthetic group; (ii) the GWYXXXE (SEQ ID NO:45, where X can be any amino acid residue) motif (corresponding to amino acid residues 278–284 of the nitric oxide synthase of *Streptomyces acidiscabies* (SEQ ID NO:2)), which functions to bind the guanidinium or hydroxy-guanidinium-containing NOS substrate; and (iii) the WSWXXXP (SEQ ID NO:46, where X can be any amino acid residue) motif (corresponding to amino acid residues 368–374 of the nitric oxide synthase of *Streptomyces acidiscabies* (SEQ ID NO:2)), which functions to interact with cofactors or substrates that can be capable of reduction/oxidaton reactions with the NOS heme center (e.g. reduced pterins such as tetrahydrofolateand tetrahydrobiopterin). The three conserved motifs described above can be combined to define a nitric oxide synthase protein or polypeptide for use in the Nitrogen-Modifying Methods of the present invention as having an amino acid sequence of SEQ ID NO:50 as follows:

(37X–174X) RCIGR (48X–67X) GWYXXXE (83X) WSWXXXP (20X–38X)

Still other suitable nitric oxide synthases for use in Nitrogen-Modifying Methods can include those having amino acid sequences that contain amino acid motifs that are conserved in nitric oxide synthases from a variety of sources. Suitable sources of nitric oxide synthases can include, for example, *Bacillus anthracis, Bacillus cereus, Bacillus subtilis, Bacillus halodurans, Staphylococcus aureus, Staphylococcus epidermidis, Deinococcus radiodurans, Mus musculus, Streptomyces acidiscabies, Streptomyces scabies Streptomyces turgidiscabies,* and *Streptomyces avermitilis*. An alignment of the nitric oxide synthases from these organisms is shown in FIG. 6.

The various conserved regions of the nitric oxide synthases from *Streptomyces acidiscabies, Streptomyces scabies Streptomyces turgidiscabies,* and *Streptomyces avermitilis* are described below in Table 2 (below).

TABLE 2

Conserved Regions of the Nitric Oxide Synthase Proteins or Polypeptides From *Streptomyces acidiscabies, Streptomyces scabies, Streptomyces turgidiscabies,* and *Streptomyces avermitilis*

| Location[1] | Motif | |
|---|---|---|
| 82–89 | TGTYRHTT | (SEQ ID NO: 29) |
| 95–102 | GARVAWRN | (SEQ ID NO: 30) |
| 105–112 | RCIGRLYW | (SEQ ID NO: 31) |
| 152–156 | VFAPD | (SEQ ID NO: 32) |
| 166–170 | WNEQL | (SEQ ID NO: 33) |
| 208–214 | PFDVLPL | (SEQ ID NO: 34) |
| 251–257 | LRWHAVP | (SEQ ID NO: 35) |
| 274–286 | APFNGWYMGTEIG | (SEQ ID NO: 36) |
| 319–326 | DRALVELN | (SEQ ID NO: 37) |
| 329–333 | VLHSF | (SEQ ID NO: 38) |
| 366–374 | ADWSWIVPP | (SEQ ID NO: 39) |
| 380–385 | TPVFHR | (SEQ ID NO: 40) |

[1]The "Location" refers to the range of amino acid residues as corresponding to the amino acid sequence of the NOS from *Streptomyces acidiscabies* (i.e., SEQ ID NO: 2).

The information presented in Table 2 can be combined to define a nitric oxide synthase protein or polypeptide for use in the Nitrogen-Modifying Methods of the present invention as having an amino acid sequence of SEQ ID NO:48 (with X being any amino acid) as follows:

(81X–151X)TGTYRHTT(5X)GARVAWRN(2X)RCIGRLYW(39X)VFAPD(9X)WNEQL(37X)

PFDVLPL(36X)LRWHAVP(16X)APFNGWYMGTEIG(32X)DRALVELN(2X)VLHSF(32X)AD

WSWIVPP(5X)TPVFHR(15X–30X)

The various conserved regions of the nitric oxide synthases from *Bacillus anthracis*, *Bacillus cereus*, *Bacillus subtilis*, *Staphylococcus aureus*, *Staphylococcus epidermidis*, *Deinococcus radiodurans*, *Mus musculus*, *Streptomyces acidiscabies*, *Streptomyces scabies Streptomyces turgidiscabies*, and *Streptomyces avermitilis* are described below in Table 3 (below).

TABLE 3

Conserved Regions of the Nitric Oxide
Synthase Proteins or Polypeptides From
Eleven Different Sources[3]

| Location[1] | Motif[2] | |
|---|---|---|
| 97–103 | 23AWRN4 | (SEQ ID NO:41) |
| 105–110 | RC5GR6 | (SEQ ID NO:42) |
| 169–174 | QL5RYA | (SEQ ID NO:43) |

[1]The "Location" refers to the range of amino acid residues as corresponding to the amino acid sequence of the NOS from *Streptomyces acidiscabies* (i.e., SEQ ID NO:2).
[2]The numerals used in the Motifs represent alternative amino acid residues as follows: 2 = R or K; 3 = M or V; 4 = S or A; 5 = I or V; and 6 = L or I
[3]The twelve sources include *Bacillus anthracis, Bacillus cereus, Staphylococcus aureus, Staphylococcus epidermidis, Bacillus halodurans, Bacillus subtilis* subsp. *subtilis, Deinococcus radiodurans, Streptomyces acidiscabies, Streptomyces scabies, Streptomyces turgidiscabies, Streptomyces avermitilis,* and *Mus musculus.*

The information presented in Table 3 can be combined to define a nitric oxide synthase protein or polypeptide for use in the Nitrogen-Modifying Methods of the present invention as having an amino acid sequence of SEQ ID NO:49 (with X being any amino acid and 2, 3, 4, 5 and 6 having the same definitions as for Table 3) as follows:

(29X–166X)23AWRN4(1X)RC5GR6(52X–58X)QL5RYA(220X–243X)

In view of the information contained herein regarding conserved regions of the various nitric oxide synthases, a suitable nitric oxide synthase for use in the Nitrogen-Modifying Methods of the present invention can include proteins or polypeptides having an amino acid motif having an amino acid sequence of one of the following: SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22; SEQ ID NO:23; SEQ ID NO:24; SEQ ID NO:25; SEQ ID NO:26; SEQ ID NO:27; SEQ ID NO:28; SEQ ID NO:29; SEQ ID NO:30; SEQ ID NO:31; SEQ ID NO:32; SEQ ID NO:33; SEQ ID NO:34; SEQ ID NO:35; SEQ ID NO:36; SEQ ID NO:37; SEQ ID NO:38; SEQ ID NO:39; SEQ ID NO:40; SEQ ID NO:41; SEQ ID NO:42; SEQ ID NO:43; SEQ ID NO:44; SEQ ID NO:45; SEQ ID NO:46; and/or combinations thereof. More particularly, the nitric oxide synthase used in the Nitrogen-Modifying Methods of the present invention can have an amino acid sequence of SEQ ID NO:47, SEQ ID NO:48, SEQ ID NO:49, or SEQ ID NO:50.

As referenced in the Nitrogen-Modifying Methods of the present invention, a suitable nitrogen group can include a nitro group (i.e., $NO_2$) or a nitroso group (i.e., NO). The reaction catalyzed by the nitric oxide synthase, whereby the nitrogen group is added to the target moiety, can be a nitration reaction or a nitrosylation reaction.

The Nitrogen-Modifying Methods of the present invention can be used to yield various types of nitrogen-modified compounds. An example of a class of nitrogen-modified compounds of the present invention are secondary metabolites. As used herein, the term "secondary metabolite" refers to those compounds of an organism that are not essential for normal growth, development, or reproduction of that organism. Suitable examples of such secondary metabolites include alkaloids, terpenoids, aliphatic organic acids, aromatic organic acids, heteroaromatic organic acids, phenols, irridoids, steroids, volatile oils, resins, balsams, β-lactams, aminoglycosides, macrolides, tetracyclines, and saponins. Other suitable nitrogen-modified compounds can include polyketides, peptides (including, for example, non-ribosomal peptides), and phytotoxins (including, for example, thaxtomin). Still other suitable nitrogen-modified compounds can include herbicides, nematicides, fungicides, insecticides, antibiotics (e.g., chloramphenicol), and anti-cancer agents (e.g., L-alanosine). Additional suitable nitrogen-modified compounds can include high-energy materials. Examples of such high-energy materials include nitroglycerin, trinitrotoluene, pentaerythriotoltetranitrate, cyclotrimethylenetrinitramine, and ammonium nitrate fertilizer.

Various moieties of compounds can be targeted for addition of a nitrogen group. An example of a target moiety (as defined by the present invention) can include an electron-rich aromatic group. Particular target moieties can include a phenyl moiety or an indole moiety, and more particularly a tryptophanyl moiety.

EXAMPLES

Example 1

Thaxtomin Production

*Streptomyces turgidiscabies* cultures were grown in oat bran broth or oat meal broth (Healy et al., *Mol. Micro.* 38:794–804 (2000); and Goyer et al., *Phytopathology* 88:442–445 (1998), which are hereby incorporated by reference in their entirety) inoculated with spores. After shaking at 150 rpm and 25° C. for 5–9 days the cultures were filtered and dry weight of the mycelia was measured. Thaxtomin was extracted from the filtrate with ethyl acetate, dried, redissolved in methanol, and quantified using HPLC (column: 5 μm C18; 250×4.6 mm; mobile phase: MeCN: $H_2O$:TFA (40:60:0.1)). In experiments investigating the suppression of thaxtomin production in the presence of L-NAME, this NOS inhibitor was dissolved in water, filter-sterilized, and added at the time of inoculation.

Example 2

$^{15}$N Feeding Studies

NMR analysis was conducted on thaxtomin A extracted from cultures fed either L-Arginine-guanidino-$^{15}N_2$.HCl (Cambridge Isotope Laboratories), or $^{15}NH_4NO_3$ (Aldrich). $^{15}NH_4NO_3$ was added to oat bran broth at the time of inoculation with spores of *S. turgidiscabies*, whereas L-Arg-guanidino-$^{15}N_2$.HCl was added just prior to the onset of thaxtomin biosynthesis (4–5 days after inoculation). Purified thaxtomin A dissolved in $CD_3OD$ was analyzed on a Varian VXR-400S spectrometer equipped with a Nalorac broadband probe affording observation of $^{15}$N at 40.5 MHZ. Spectra were referenced externally by observing the $^{15}$N signal of formamide (90% solution in DMSO) and then acquiring sample spectra with identical parameter sets. A conventional chemical shift scale (liquid $NH_3$=0 ppm) was established by referencing the formamide signal to its reported value of 112 ppm (Martin et al., *J. Nat. Prod.* 63:543–585 (2000), which is hereby incorporated by reference in its entirety).

Example 3

Molecular Biology

DNA and RNA manipulation were performed using standard techniques. Transformation of *S. turgidiscabies* was performed using polyethylene glycol (PEG) mediated transformation of *S. turgidiscabies* protoplasts using plasmid vectors propagated in *E. coli* ET12567 (MacNeil et al., *Gene* 111:61–68 (1992), which is hereby incorporated by reference in its entirety). *Streptomyces turgidiscabies* p2XNOS single cross-over transformants (apramycin resistant, thiostrepton resistant) were grown for three generations of growth and sporulation on minimal medium containing thiostrepton, after which colonies containing double cross-over (apramycin sensitive, thiostrepton resistant) recombination events were screened. Expression of nos was induced in the complemented Δnos strain by addition of 10 μg ml$^{-1}$ thiostrepton in a 5 mL oat bran culture 3 days following inoculation.

Example 4

A Bacterial Nitric Oxide Synthase Functions to Nitrate a Peptide Phytotoxin

Figure 1:
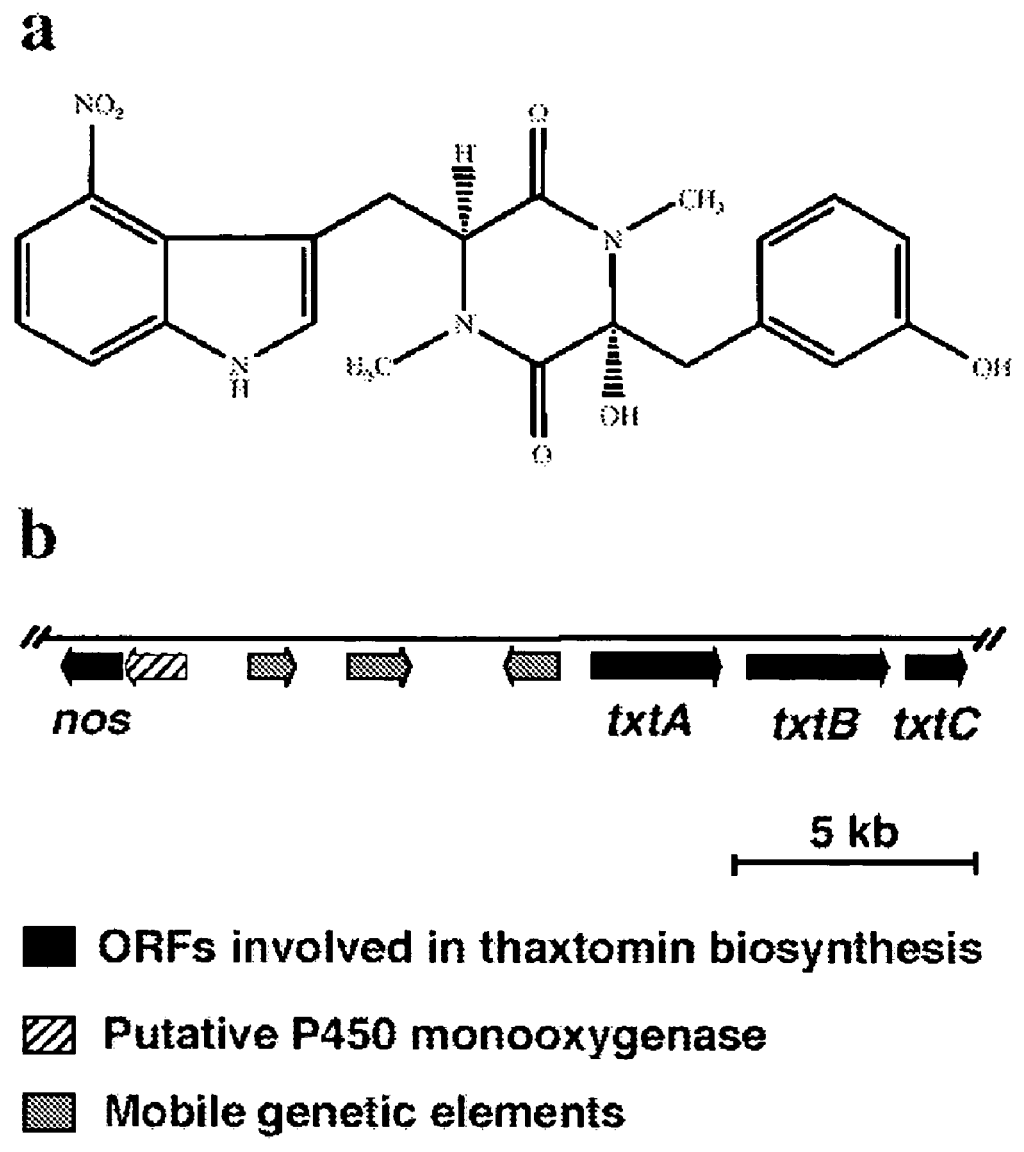

Plant pathogenic *Streptomyces* species are the causal agents of potato scab disease, a globally important disease of potato. Pathogenicity depends on production of a class of dipeptide phytotoxins called thaxtomins (Healy et al., *Mol. Micro.* 38:794–804 (2000), which is hereby incorporated by reference in its entirety). While investigating the molecular genetics of plant pathogenicity in *Streptomyces* species, it was discovered that a gene with high sequence similarity to mammalian and bacterial NOSs. The location of this gene on a pathogenicity island that mobilizes among species to confer thaxtomin biosynthetic ability and its proximity to two nonribosomal peptide synthases of the thaxtomin biosynthetic pathway suggests that the NOS participates in nitration of thaxtomins (FIGS. 1A–1B). The DNA sequence of the nos genes in *S. turgidiscabies, S. acidiscabies* and *S. scabies,* all of which produce thaxtomin A, is highly conserved (Genbank accessions AY204507–AY204509). Conservation of nearly all key residues known in mammalian and *B. subtilis* NOSs that participate in cofactor-binding, substrate-binding and catalysis by *S. turgidiscabies* NOS (stNOS) suggests that stNOS is capable of producing NO from L-Arg (FIG. 2). As in other bacterial NOSs, the reductase domain and CaM binding site typical of mammalian NOSs are absent in stNOS. However, stNOS has an extended N-terminal region that is lacking in other bacterial proteins (FIG. 2). A mammalian NOS zinc-binding motif absent in the N-termini of other bacterial NOSs may be conserved in some of the pathogenic *Streptomyces* spp. NOSs.

To determine if stNOS is required for production of thaxtomin A, nos was deleted from *S. turgidiscabies* (FIGS. 3A–3B). The Δnos strain produced only trace amounts of thaxtomin A (0.20±0.02 μg ml$^{-1}$; standard deviation reported, n=3 for each strain tested) compared to the wild-type strain (18.31±0.92 μg ml$^{-1}$). De-nitrothaxtomin was not detectable in the medium. Deletion of nos did not affect bacterial growth, but did eliminate disease on potato tubers. Complemention of nos was achieved by expressing nos using the thiostrepton-inducible promoter on plasmid pIJ8600, which integrates into the chromosomal ϕC31 phage attachment site (FIG. 3B) (Sun et al., *Microbiology* 145: 2221–2227 (1999), which is hereby incorporated by reference in its entirety). The complemented strain Δnos pIJ8600NOS increased the amount of thaxtomin A produced over 25 fold (3.68±0.06 μg ml$^{-1}$ thaxtomin A) compared to the empty vector control strain Δnos pIJ8600 (0.13±0.01 μg ml$^{-1}$). Expression of nos in the *S. turgidiscabies* wild-type strain was confirmed using reverse transcriptase (RT)-PCR (FIG. 3C). nos was not expressed in the Δnos or Δnos pIJ8600 strains, but expression was restored in the complemented strain Δnos pIJ8600NOS.

Figure 4:
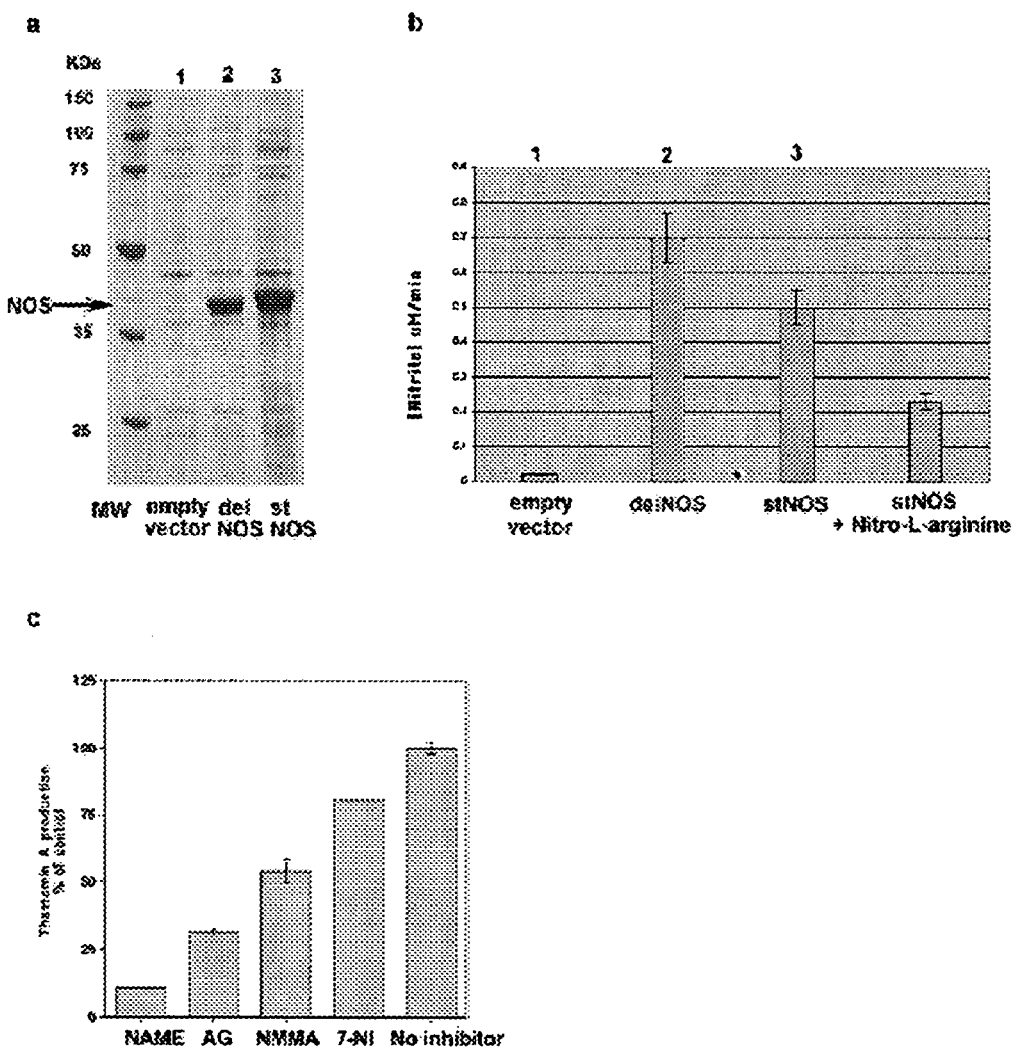

For stNOS to be responsible for thaxtomin nitration, stNOS should have NO synthase activity. Further, this activity and thaxtomin production should be arginine dependent. As predicted, overexpressed stNOS in *E. coli* produced nitrite from N-hydroxy-L-arginine in a standard NOS assay (FIGS. 4A–4B). N-hydroxy-L-arginine is an intermediate unique to the NOS catalytic reaction and nitrite represents the end product of NO reacting in oxygenated solution. NO synthase activity of the recombinant stNOS was inhibited by the selective NOS inhibitor nitro-L-arginine (FIG. 4B); nitro-L-arginine is the active form of Nitro-L-arginine methyl ester (NAME). NOS inhibitors were also evaluated for their effect on thaxtomin A production by *S. turgidiscabies*. NAME greatly suppressed thaxtomin production by *S. turgidiscabies* ($IC_{50}$=15 μM) but did not affect bacterial growth (FIG. 4C). Inhibition of thaxtomin production occurred at concentrations commensurate with the binding affinities of NAME to mammalian NOSs (Alderton et al., *Biochem J.* 357:593–615 (2001); and Southan et al., *Biochem. Pharm.* 51,383–394 (1996), which are hereby incorporated by reference in their entirety). The other three NOS inhibitors tested also suppressed thaxtomin A production but to a lesser extent than NAME. Thus, inhibitors specific for the conserved NOS active center greatly curtail both NO synthase activity from recombinant stNOS in vitro and thaxtomin production in vivo.

Figure 5:
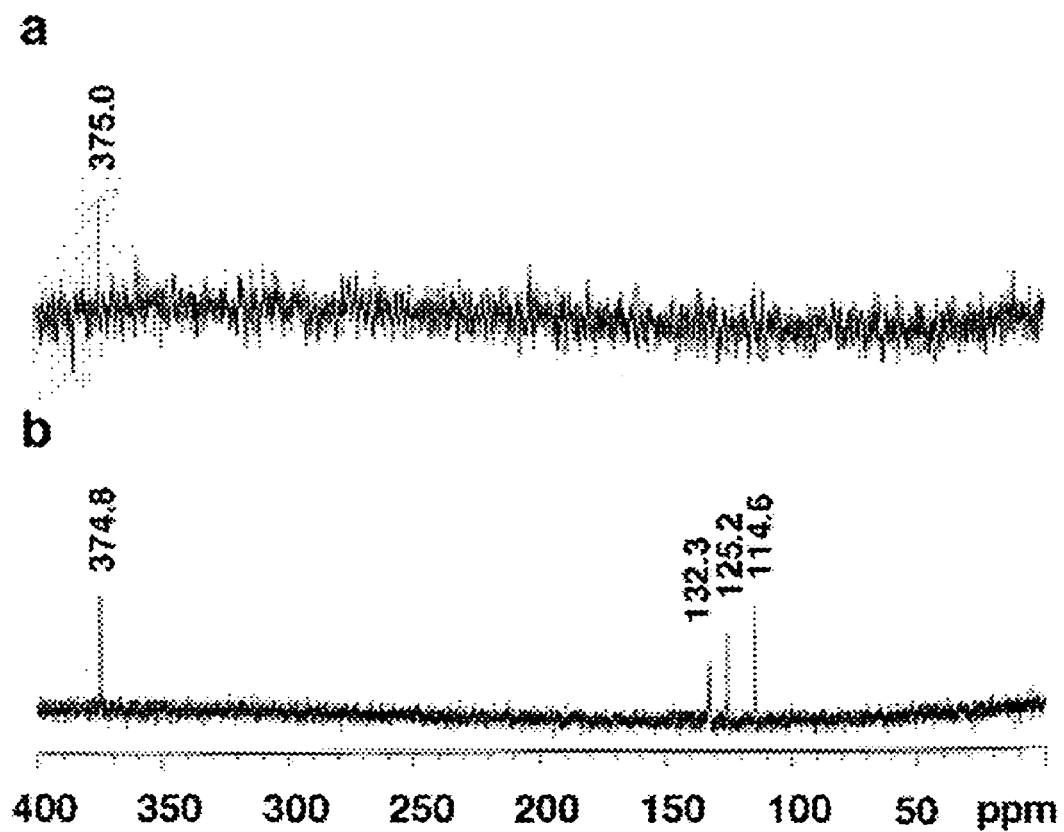

Mammalian NOSs convert a terminal guanidino nitrogen of the L-Arg substrate to an oxidized nitrogen species. One model for the role of stNOS in nitration of thaxtomin predicts that the nitrate nitrogen derives from a terminal guanidino nitrogen of L-Arg. A $^{15}$N feeding study was conducted; either L-Arg-guanidino-$^{15}N_2$.HCl or $^{15}NH_4NO_3$ was added to cultures of *S. turgidiscabies* under conditions that induce thaxtomin production. $^{15}$N-NMR analysis of thaxtomin A extracted from cultures fed the L-Arg-guanidino-$^{15}N_2$.HCl detected label only at the 4-nitro position, while in thaxtomin A extracted from control cultures fed $^{15}NH_4NO_3$, all of the four nitrogens in thaxtomin were equally labeled (FIGS. 5A–5B). Electron impact ionization mass spectra of thaxtomin A also indicated specific incorporation of $^{15}$N into the nitro group when the cultures were fed L-Arg-guanidino-$^{15}N_2$.HCl. There is no known enzymatic process other than NOS activity that converts L-Arg terminal guanidino nitrogen to an oxidized nitrogen species capable of nitration. These results provide definitive evidence for the role of stNOS in nitration of thaxtomin.

The specific nitration of a tryptophanyl moiety for biosynthesis is an unprecedented metabolic role for a NOS protein, although mammalian NOS production of nitroxyl (NO⁻) and superoxide ($O_2^-$) is well characterized and such products could readily lead to nitrating species (Alderton et al., *Biochem J.* 357:593–615 (2001), which is hereby incorporated by reference in its entirety). Biosynthetic nitration reactions are rare and usually involve the oxidation of an amine (Carter et al, *J. Chem. Soc. Chem. Commun.* 17:1271–1273 (1989), which is hereby incorporated by reference in its entirety). The chemical mechanism of a NOS-mediated nitration may be complex because NO is unlikely to react directly with indole (Patel et al., *Biochemica. Biophys. Acta.* 1411:385–400 (1999); Koppenol, *Free Rad. Biol. Med.* 25:385–391 (1998); Hughes, *Biochim. Biophys. Acta* 1411:263–272 (1999); and Ridd, *Acta Chemica. Scand.* 52:11–22 (1998), which are hereby incorporated by reference in their entirety). Nevertheless, readily oxidized forms of NO, such as nitrosonium (NO⁺), peroxynitrite (ONOO⁻), nitronium ($NO_2^+$), or nitrogen dioxide ($NO_2$) actively nitrate aromatic amino acids (Patel et al., *Biochemica. Biophys. Acta.* 1411:385–400 (1999); Koppenol, *Free Rad. Biol. Med.* 25:385–391 (1998); Hughes, *Biochim. Biophys. Acta* 1411:263–272 (1999); and Ridd, *Acta Chemica. Scand.* 52:11–22 (1998), which are hereby incorporated by reference in their entirety), and such reactions have been implicated in mammalian signaling (Packer, *Methods Enzymol.* 268 (1996); and Ischiropoulos, *Free Rad. Biol. Med.* 33 (2002), which are hereby incorporated by reference in their entirety). Given the high reactivities of these nitrogen oxide species towards tryptophan, the substrate nitrated likely contains indole; whether this substrate is tryptophan, an immediate precursor of thaxtomin, or some other intermediate, is currently under investigation. Interestingly, tryptophan nitration by peroxynitrite results primarily in modification at the indole 6-position (Alvarez et al., *Chem. Res. Toxicol.* 9:390–396 (1996), which is hereby incorporated by reference in its entirety). Thus, production of a 4-nitrotryptophanyl moiety (FIG. 1A) suggests some enzymatic control of the nitration reaction. Nevertheless, minimal thaxtomin production in the Δnos strain indicates that diffusible nitration agents produced by other cellular processes can react productively with a thaxtomin precursor.

Conservation of residues in the heme pocket, pterin site, and substrate access channel among the bacterial NOSs suggest a common function for prokaryotic enzymes and distinguish them from their mammalian counterparts (FIG. 2). A distinguishing catalytic feature between mammalian NOS and bsNOS is that the bacterial protein retains product NO coordinated to its heme iron 10–20× longer than the mammalian enzymes (Adak et al., *J. Biol. Chem.* 277: 16167–16171 (2002), which is hereby incorporated by reference in its entirety)). This correlates to a more sequestered immediate heme pocket that appears conserved in stNOS (Pant et al., *Biochemistry* 41:11071–11079 (2002), which is hereby incorporated by reference in its entirety). Perhaps a slower NO release allows bacterial proteins to direct NO reactivity by either sequestering NO close to the site of substrate binding, or by facilitating reaction with $O_2$. It is suggested that other bacterial NOSs may also participate in the biosynthesis of secondary metabolites through nitration of an amino acid or peptide substrate. Truncated NOSs have only been discovered in a subset of Gram-positive genomes and are absent from Gram-negative genomes, supporting a role for NOS proteins in secondary metabolism, rather than a signaling function essential for vitality. Nitrated compounds are produced by other bacteria and fungi (Carter et al, *J. Chem. Soc. Chem. Commun.* 17:1271–1273 (1989); Jalal et al., *Acta Crystallography* C42:733–738 (1986); and Ohba et al., *J. Antibiot.* 40:709–713 (1987), which are hereby incorporated by reference in their entirety) and at least one is likely to derive from an aromatic nitration reaction (Carter et al, *J. Chem. Soc. Chem. Commun.* 17:1271–1273 (1989), which is hereby incorporated by reference in its entirety). NOS-initiated nitrations would produce a class of compounds with unique chemical reactivity and diverse biological activities. From an evolutionary perspective, it is interesting that homologous enzymes are responsible for biosynthetic nitration reactions in bacteria and NO signaling in mammals.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

---

What is claimed:

1. An isolated nucleic acid molecule encoding a nitric oxide synthase, wherein the nucleic acid molecule:
   (i) comprises the nucleotide sequence of SEQ ID NO:5;
   (ii) comprises a nucleotide sequence that hybridizes to SEQ ID NO:5 under high stringency conditions comprising 4–5×SSC/0.1% w/v SDS at 54° C. for 1–3 hours and 4×SSC at 65° C., followed by a washing in 0.1×SSC at 65° C. for about one hour;
   (iii) comprises a nucleotide sequence that has greater than 95 percent sequence homology to SEQ ID NO:5 ;
   (iv) comprises a nucleotide sequence that has greater than 95 percent sequence homology to SEQ ID NO:5 and that encodes a nitric oxide synthase comprising a protein or polypeptide having the amino acid sequence of SEQ ID NO:47; or
   (v) comprises a nucleotide sequence that encodes the amino acid sequence of SEQ ID NO:6.

2. The isolated nucleic acid molecule according to claim 1, wherein the nucleic acid molecule comprises the nucleotide sequence of SEQ ID NO:5.

3. The isolated nucleic acid molecule according to claim 1, wherein the nucleic acid molecule comprises a nucleotide sequence that hybridizes to SEQ ID NO:5 under high stringency conditions comprising 4–5×SSC/0.1% w/v SDS at 54° C. for 1–3 hours and 4×SSC at 65° C., followed by a washing in 0.1×SSC at 65° C. for about one hour.

4. The isolated nucleic acid molecule according to claim 1, wherein the nucleic acid molecule comprises a nucleotide sequence that has greater than 95 percent sequence homology to SEQ ID NO:5.

5. The isolated nucleic acid molecule according to claim 1, wherein the nucleic acid molecule comprises a nucleotide sequence that has greater than 95 percent sequence homology to SEQ ID NO:5 and that encodes a nitric oxide synthase comprising a protein or polypeptide having the amino acid sequence of SEQ ID NO:47.

6. The isolated nucleic acid molecule according to claim 1, wherein the nitric oxide synthase is from a *Streptomyces* species selected from the group consisting of *Streptomyces acidiscabies*, *Streptomyces scabies*, *Streptomyces turgidiscabies*, *Streptomyces avermitilis*, and *Streptomyces ipomoea*.

7. The isolated nucleic acid molecule according to claim 1, wherein the nucleic acid is DNA.

8. An expression system comprising a vector into which is inserted the nucleic acid molecule according to claim 1.

9. The expression system according to claim 8, wherein the nucleic acid molecule is inserted in sense orientation.

10. An isolated host cell comprising the nucleic acid molecule according to claim 1.

11. The host cell according to claim 10, wherein the host cell is selected from the group consisting of a bacterial cell, a yeast cell, a fungal cell, an insect cell, a plant cell, and a mammalian cell.

12. The host cell according to claim 11, wherein the bacterial cell is *Streptomyces*, *Bacillus*, *Escherichia*, *Brevibacterium*, *Microbacterium*, *Nocardia*, or *Rhodococcus*.

13. A method of recombinantly producing a nitric oxide synthase in an isolated host cell, said method comprising:
   transforming an isolated host cell with at least one nucleic acid molecule according to claim 1, said transforming being performed under conditions suitable for expression of the nitric oxide synthase; and
   isolating the nitric oxide synthase.

14. The method according to claim 13, wherein the host cell is selected from the group consisting of a bacterial cell, a yeast cell, a fungal cell, an insect cell, a plant cell, and a mammalian cell.

15. The method according to claim 14, wherein the bacterial cell is *Streptomyces, Bacillus, Escherichia, Brevibacterium, Microbacterium, Nocardia*, or *Rhodococcus*.

16. The method according to claim 14, wherein the yeast cell is *Saccharomyces*.

17. The method according to claim 14, wherein the fungal cell is *Aspergillus, Cephalosporium*, or *Penicillium*.

18. The isolated nucleic acid molecule according to claim 1, wherein the nucleic acid molecule comprises a nucleotide sequence that encodes the amino acid sequence of SEQ ID NO:6.

* * * * *

SEQUENCE LISTING

```
<160> NUMBER OF SEQ ID NOS: 59

<210> SEQ ID NO 1
<211> LENGTH: 1203
<212> TYPE: DNA
<213> ORGANISM: Streptomyces acidiscabies

<400> SEQUENCE: 1
gtgacctccg aagtcgctct gggcccttcc ttgcccgccc cgtccccgac agcgtgcccg      60
gcactggggc ccgattcgtc ccttggcccg gtcccgtcgg cggaaccggc gacgccgcag     120
tcctgcggcg tcgccgatcc aaatgaggct gaggagttcc tgcgccagtt ccacgcggag     180
cagtccgatc agcccgtccc gctcgcccgg cgcctggagc aggtccgcgc cgccatcgac     240
gccacgggca cctaccggca caccaccgcc gagctcgtgt acggtgcccg cgtcgcgtgg     300
cgcaactcca gtcgctgcat cggccgcctg tactggaaca gcctgcgcgt cctggaccgc     360
```

-continued

```
cgggacgcca cagcccccga tgagatccac cggcacttgt gcacgcacct gcgccaggcg    420
accaacggcg ggcgcatcag gccggtgatt tcggtcttcg ccccggactc ccccggccgg    480
cccggcccgc aggtgtggaa cgagcagctc atccggtacg ccggctaccg ccgcgacgac    540
ggcaccgtgc tcggtgaccc cgcgcaccgc cgacctcaccg aggccatcct ccgcctcggc    600
tggcagggct gccccaagg gccgttcgac gtcctgcccc tggtcatcga caccccgac     660
gacaaacccc ggttcttcga gctgccgcgg gagctggtct tggaggtccc tatcacccac    720
cccgacgtcc cacgcctggc cgaactgggc ctgcgctggc acgccgtacc cgtcatctcc    780
aacatgcgcc tacgcatcgg cgggatggac tacccgctcg ccccgttcaa cggctggtac    840
atgggcacgg agatcggcgc ccgcaacctc gtcgacgagg accgctacaa catgctcccc    900
gccgtcgccc cctgcctcca gctggacacc accagcgagt caaccctgtg gcgcgaccgc    960
gccctggtcg agctcaacgt cgccgtcctg cactccttcg aggccgcagg tgtccggatc   1020
agcgaccacc acgaggagtc ccggcgcttc ctcgcccacc tggccaagga ggaacgccag   1080
ggccgcaccg tatccgcaga ctggagctgg atcgtccccc cgctctccgg cggcatcacc   1140
cccgtgttcc accgttacta cgacaacgtc gaccagcgcc caacttcta ccccaccag   1200
tga                                                                 1203
```

<210> SEQ ID NO 2
<211> LENGTH: 400
<212> TYPE: PRT
<213> ORGANISM: Streptomyces acidiscabies

<400> SEQUENCE: 2

```
Met Thr Ser Glu Val Ala Leu Gly Pro Ser Leu Pro Ala Pro Ser Pro
 1               5                  10                  15

Thr Ala Cys Pro Ala Leu Gly Pro Asp Ser Ser Leu Gly Pro Val Pro
             20                  25                  30

Ser Ala Glu Pro Ala Thr Pro Gln Ser Cys Gly Val Ala Asp Pro Asn
         35                  40                  45

Glu Ala Glu Glu Phe Leu Arg Gln Phe His Ala Glu Gln Ser Asp Gln
     50                  55                  60

Pro Val Pro Leu Ala Arg Arg Leu Glu Gln Val Arg Ala Ala Ile Asp
 65                  70                  75                  80

Ala Thr Gly Thr Tyr Arg His Thr Thr Ala Glu Leu Val Tyr Gly Ala
                 85                  90                  95

Arg Val Ala Trp Arg Asn Ser Arg Cys Ile Gly Arg Leu Tyr Trp
            100                 105                 110

Asn Ser Leu Arg Val Leu Asp Arg Arg Asp Ala Thr Ala Pro Asp Glu
        115                 120                 125

Ile His Arg His Leu Cys Thr His Leu Arg Gln Ala Thr Asn Gly Gly
    130                 135                 140

Arg Ile Arg Pro Val Ile Ser Val Phe Ala Pro Asp Ser Pro Gly Arg
145                 150                 155                 160

Pro Gly Pro Gln Val Trp Asn Glu Gln Leu Ile Arg Tyr Ala Gly Tyr
                165                 170                 175

Arg Arg Asp Asp Gly Thr Val Leu Gly Asp Pro Arg Thr Ala Asp Leu
            180                 185                 190

Thr Glu Ala Ile Leu Arg Leu Gly Trp Gln Gly Cys Pro Gln Gly Pro
        195                 200                 205

Phe Asp Val Leu Pro Leu Val Ile Asp Thr Pro Asp Asp Lys Pro Arg
    210                 215                 220
```

```
Phe Phe Glu Leu Pro Arg Glu Leu Val Leu Glu Val Pro Ile Thr His
225                 230                 235                 240

Pro Asp Val Pro Arg Leu Ala Glu Leu Gly Leu Arg Trp His Ala Val
            245                 250                 255

Pro Val Ile Ser Asn Met Arg Leu Arg Ile Gly Gly Met Asp Tyr Pro
        260                 265                 270

Leu Ala Pro Phe Asn Gly Trp Tyr Met Gly Thr Glu Ile Gly Ala Arg
    275                 280                 285

Asn Leu Val Asp Glu Asp Arg Tyr Asn Met Leu Pro Ala Val Ala Ala
290                 295                 300

Cys Leu Gln Leu Asp Thr Thr Ser Glu Ser Thr Leu Trp Arg Asp Arg
305                 310                 315                 320

Ala Leu Val Glu Leu Asn Val Ala Val Leu His Ser Phe Glu Ala Ala
            325                 330                 335

Gly Val Arg Ile Ser Asp His His Glu Glu Ser Arg Arg Phe Leu Ala
        340                 345                 350

His Leu Ala Lys Glu Glu Arg Gln Gly Arg Thr Val Ser Ala Asp Trp
    355                 360                 365

Ser Trp Ile Val Pro Pro Leu Ser Gly Gly Ile Thr Pro Val Phe His
370                 375                 380

Arg Tyr Tyr Asp Asn Val Asp Gln Arg Pro Asn Phe Tyr Pro His Gln
385                 390                 395                 400

<210> SEQ ID NO 3
<211> LENGTH: 1203
<212> TYPE: DNA
<213> ORGANISM: Streptomyces scabies

<400> SEQUENCE: 3
gtgacctccg aagtcgctct gggcccttcc ttgcccgccc cgtccccgac agcgtgcccg     60
gcactggggc ccgattcgtc ccttggcccg gtccgtcgg cggaaccggc gacgccgcag    120
tcctgcggcg tcgccgatcc aaatgaggct gaggagttcc tgcgccagtt ccacgcggag    180
cagtccgatc agcccgtccc gctcgcccgg cgcctggagc aggtccgcgc cgccatcgac    240
gccacgggca cctaccggca caccaccgcc gagctcgtgt acggtgcccg cgtcgcgtgg    300
cgcaactcca gtcgctgcat cggccgcctg tactggaaca gcctgcgcgt cctggaccgc    360
cgggacgcca gcccccga tgagatccac cggcacttgt gcacgcacct gcgccaggcg    420
accaacggcg ggcgcatcag gccggtgatt tcggtcttcg ccccggactc ccccggccgg    480 cccggccccgc aggtgtggaa cgagcagctc atccggtacg ccggctaccg ccgcgacgac    540
ggcaccgtgc tcggtgaccc cgcaccgcc gacctcaccg aggccatcct ccgcctcggc    600
tggcagggct gccccaagg gccgttcgac gtcctgcccc tggtcatcga caccccgac    660 gacaaacccc ggttcttcga gctgccgcgg gagctggtct tggaggtccc tatcacccac    720
cccgacgtcc cacgcctggc cgaactgggc ctgcgctggc acgccgtacc cgtcatctcc    780
aacatgcgcc tacgcatcgg cgggatggac taccgctcg ccccgttcaa cggctggtac    840
atgggcacgg agatcggcgc ccgcaacctc gtcgacgagg accgctacaa catgctcccc    900
gccgtcgccg cctgcctcca gytgacacc accagcgagt caaccctgtg gcgcgaccgc    960
gccctggtcg agctcaacgt cgccgtcctg cactccttcg aggccgcagg tgtccggatc   1020
agcgaccacc acgaggagtc ccggcgcttc ctcgcccacc tggccaagga ggaacgccag   1080
ggccgcaccg tatccgcaga ctggagctgg atcgtccccc cgctctccgg cggcatcacc   1140
```

```
cccgtgttcc accgttacta cgacaacgtc gaccagcgcc ccaacttcta cccccaccag    1200
tga                                                                  1203
```

<210> SEQ ID NO 4
<211> LENGTH: 400
<212> TYPE: PRT
<213> ORGANISM: Streptomyces scabies

<400> SEQUENCE: 4

```
Met Thr Ser Glu Val Ala Leu Gly Pro Ser Leu Pro Ala Pro Ser Pro
 1               5                  10                  15

Thr Ala Cys Pro Ala Leu Gly Pro Asp Ser Ser Leu Gly Pro Val Pro
            20                  25                  30

Ser Ala Glu Pro Ala Thr Pro Gln Ser Cys Gly Val Ala Asp Pro Asn
        35                  40                  45

Glu Ala Glu Glu Phe Leu Arg Gln Phe His Ala Glu Gln Ser Asp Gln
    50                  55                  60

Pro Val Pro Leu Ala Arg Arg Leu Glu Gln Val Arg Ala Ala Ile Asp
65                  70                  75                  80

Ala Thr Gly Thr Tyr Arg His Thr Thr Ala Glu Leu Val Tyr Gly Ala
                85                  90                  95

Arg Val Ala Trp Arg Asn Ser Arg Cys Ile Gly Arg Leu Tyr Trp
            100                 105                 110

Asn Ser Leu Arg Val Leu Asp Arg Arg Asp Ala Thr Ala Pro Asp Glu
        115                 120                 125

Ile His Arg His Leu Cys Thr His Leu Arg Gln Ala Thr Asn Gly Gly
    130                 135                 140

Arg Ile Arg Pro Val Ile Ser Val Phe Ala Pro Asp Ser Pro Gly Arg
145                 150                 155                 160

Pro Gly Pro Gln Val Trp Asn Glu Gln Leu Ile Arg Tyr Ala Gly Tyr
                165                 170                 175

Arg Arg Asp Asp Gly Thr Val Leu Gly Asp Pro Arg Thr Ala Asp Leu
            180                 185                 190

Thr Glu Ala Ile Leu Arg Leu Gly Trp Gln Gly Cys Pro Gln Gly Pro
        195                 200                 205

Phe Asp Val Leu Pro Leu Val Ile Asp Thr Pro Asp Asp Lys Pro Arg
    210                 215                 220

Phe Phe Glu Leu Pro Arg Glu Leu Val Leu Glu Val Pro Ile Thr His
225                 230                 235                 240

Pro Asp Val Pro Arg Leu Ala Glu Leu Gly Leu Arg Trp His Ala Val
                245                 250                 255

Pro Val Ile Ser Asn Met Arg Leu Arg Ile Gly Gly Met Asp Tyr Pro
            260                 265                 270

Leu Ala Pro Phe Asn Gly Trp Tyr Met Gly Thr Glu Ile Gly Ala Arg
        275                 280                 285

Asn Leu Val Asp Glu Asp Arg Tyr Asn Met Leu Pro Ala Val Ala Ala
    290                 295                 300

Cys Leu Gln Leu Asp Thr Thr Ser Glu Ser Thr Leu Trp Arg Asp Arg
305                 310                 315                 320

Ala Leu Val Glu Leu Asn Val Ala Val Leu His Ser Phe Glu Ala Ala
                325                 330                 335

Gly Val Arg Ile Ser Asp His His Glu Glu Ser Arg Arg Phe Leu Ala
            340                 345                 350
```

```
His Leu Ala Lys Glu Glu Arg Gln Gly Arg Thr Val Ser Ala Asp Trp
        355                 360                 365

Ser Trp Ile Val Pro Pro Leu Ser Gly Gly Ile Thr Pro Val Phe His
    370                 375                 380

Arg Tyr Tyr Asp Asn Val Asp Gln Arg Pro Asn Phe Tyr Pro His Gln
385                 390                 395                 400

<210> SEQ ID NO 5
<211> LENGTH: 1203
<212> TYPE: DNA
<213> ORGANISM: Streptomyces turgidscabies

<400> SEQUENCE: 5
gtgactttcg aagtcgccct gggcccttcc ttgcccgccc cgtccccgac agcgtgcccg      60
gcgctggcgc acgattcgcc cctcagtccc gtcccgtcgg cggaaccggc gacgtcgcag     120
gactgcggcg tcgccgatcc agacgaggcc gaggagttcc tgcgccagtt tcacgcggag     180
cagtccgacc aggccgtccc gctcactcgg cgcctggacc aggttcgcgc tgccatcgac     240
gccacgggca cctaccgtca taccaccgcc gagctcgtgt tcggtgcccg tgtcgcgtgg     300
cgcaactcca gtcgctgtat cggccgcctg tactggaaca gcctgcgcgt cctggaccgc     360
cgggacacca gcccccga ggtaatccac cggcacctt gcacgcacct gcgccaggcg     420
accaacggtg gcgtatcag gccggtgatt tcggtcttcg ccccggacgc acccagccga     480
cccggcccgc gggtgtggaa cgagcaactc gtccggtacg ccggccaccg tcgcgacgac     540
ggcaccgtac tcggcgaccc gcgatctgcc gacctcaccg aggccatccg cggcctcgga     600
tggcagggag ccgccaagg ccgttcgac gtcctgcccc tggtcatcga cgcccacgac     660
gacaaaccgc ggttcttcga gctgccgcgg gaggttgtcc tggaggtccc tatcacccac     720
cccgacgtcc cacgactggc cgaactctgc ctgcgctggc acgccgtacc cgttatctcc     780
aacatgcgcc tgcgtatcgg cggggtggac taccccctcg ccccgttcaa cggctggtac     840
atgggcacgg agatcggcgt ccgtaacctc gtcgacgagg cccgctacaa cctgctcccc     900
gccgtggccg cctgcctcca gttggacacc accagcgagt ccaccctgtg gcgtgaccgc     960
gctctggtcg aactcaacgt tgccgtcttg cactcttcg cggccgcagg cgtccggatc    1020
agtgaccacc acgaggagtc ccggcgcttc ctcgcccacc tgaccaagga ggaacgccag    1080
ggccgcaccg tacccgcgga ctggagctgg atcgtccctc cgctttccag cggcatcacc    1140
cccgtcttcc accgctacta cgacaacgcc gaccagcgcc caactttta ccctcatcag    1200 tga                                                                  1203

<210> SEQ ID NO 6
<211> LENGTH: 400
<212> TYPE: PRT
<213> ORGANISM: Streptomyces turgidscabies

<400> SEQUENCE: 6

Met Thr Phe Glu Val Ala Leu Gly Pro Ser Leu Pro Ala Pro Ser Pro
  1               5                  10                  15

Thr Ala Cys Pro Ala Leu Ala His Asp Ser Pro Leu Ser Pro Val Pro
             20                  25                  30

Ser Ala Glu Pro Ala Thr Ser Gln Asp Cys Gly Val Ala Asp Pro Asp
         35                  40                  45

Glu Ala Glu Glu Phe Leu Arg Gln Phe His Ala Glu Gln Ser Asp Gln
     50                  55                  60
```

```
Ala Val Pro Leu Thr Arg Arg Leu Asp Gln Val Arg Ala Ala Ile Asp
 65                  70                  75                  80

Ala Thr Gly Thr Tyr Arg His Thr Thr Ala Glu Leu Val Phe Gly Ala
                 85                  90                  95

Arg Val Ala Trp Arg Asn Ser Ser Arg Cys Ile Gly Arg Leu Tyr Trp
            100                 105                 110

Asn Ser Leu Arg Val Leu Asp Arg Arg Asp Thr Thr Ala Pro Glu Val
        115                 120                 125

Ile His Arg His Leu Cys Thr His Leu Arg Gln Ala Thr Asn Gly Gly
130                 135                 140

Arg Ile Arg Pro Val Ile Ser Val Phe Ala Pro Asp Ala Pro Ser Arg
145                 150                 155                 160

Pro Gly Pro Arg Val Trp Asn Glu Gln Leu Val Arg Tyr Ala Gly His
                165                 170                 175

Arg Arg Asp Asp Gly Thr Val Leu Gly Asp Pro Arg Ser Ala Asp Leu
            180                 185                 190

Thr Glu Ala Ile Arg Gly Leu Gly Trp Gln Gly Gly Arg Gln Gly Pro
        195                 200                 205

Phe Asp Val Leu Pro Leu Val Ile Asp Ala His Asp Asp Lys Pro Arg
210                 215                 220

Phe Phe Glu Leu Pro Arg Glu Val Val Leu Glu Val Pro Ile Thr His
225                 230                 235                 240

Pro Asp Val Pro Arg Leu Ala Glu Leu Cys Leu Arg Trp His Ala Val
                245                 250                 255

Pro Val Ile Ser Asn Met Arg Leu Arg Ile Gly Gly Val Asp Tyr Pro
            260                 265                 270

Leu Ala Pro Phe Asn Gly Trp Tyr Met Gly Thr Glu Ile Gly Val Arg
        275                 280                 285

Asn Leu Val Asp Glu Ala Arg Tyr Asn Leu Leu Pro Ala Val Ala Ala
290                 295                 300

Cys Leu Gln Leu Asp Thr Thr Ser Glu Ser Thr Leu Trp Arg Asp Arg
305                 310                 315                 320

Ala Leu Val Glu Leu Asn Val Ala Val Leu His Ser Phe Ala Ala Ala
                325                 330                 335

Gly Val Arg Ile Ser Asp His His Glu Glu Ser Arg Arg Phe Leu Ala
            340                 345                 350

His Leu Thr Lys Glu Glu Arg Gln Gly Arg Thr Val Pro Ala Asp Trp
        355                 360                 365

Ser Trp Ile Val Pro Pro Leu Ser Ser Gly Ile Thr Pro Val Phe His
370                 375                 380

Arg Tyr Tyr Asp Asn Ala Asp Gln Arg Pro Asn Phe Tyr Pro His Gln
385                 390                 395                 400

<210> SEQ ID NO 7
<211> LENGTH: 19
<212> TYPE: PRT
<213> ORGANISM: Artificial Sequence
<220> FEATURE:
<223> OTHER INFORMATION: Description of Artificial Sequence: Peptide

<400> SEQUENCE: 7

Glu Val Ala Leu Gly Pro Ser Leu Pro Ala Pro Ser Pro Thr Ala Cys
  1               5                  10                  15

Pro Ala Leu
```

```
<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence:  Peptide

<400> SEQUENCE: 8

Pro Val Pro Ser Ala Glu Pro Ala Thr
 1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence:  Peptide

<400> SEQUENCE: 9

Cys Gly Val Ala Asp Pro
 1               5

<210> SEQ ID NO 10
<211> LENGTH: 16
<212> TYPE: PRT
<213> ORGANISM: Artificial Sequence
<220> FEATURE:
<223> OTHER INFORMATION: Description of Artificial Sequence:  Peptide

<400> SEQUENCE: 10

Glu Ala Glu Glu Phe Leu Arg Gln Phe His Ala Glu Gln Ser Asp Gln
 1               5                  10                  15

<210> SEQ ID NO 11
<211> LENGTH: 20
<212> TYPE: PRT
<213> ORGANISM: Artificial Sequence
<220> FEATURE:
<223> OTHER INFORMATION: Description of Artificial Sequence:  Peptide

<400> SEQUENCE: 11

Gln Val Arg Ala Ala Ile Asp Ala Thr Gly Thr Tyr Arg His Thr Thr
 1               5                  10                  15

Ala Glu Leu Val
            20

<210> SEQ ID NO 12
<211> LENGTH: 28
<212> TYPE: PRT
<213> ORGANISM: Artificial Sequence
<220> FEATURE:
<223> OTHER INFORMATION: Description of Artificial Sequence:  Peptide

<400> SEQUENCE: 12

Gly Ala Arg Val Ala Trp Arg Asn Ser Ser Arg Cys Ile Gly Arg Leu
 1               5                  10                  15

Tyr Trp Asn Ser Leu Arg Val Leu Asp Arg Arg Asp
            20                  25

<210> SEQ ID NO 13
<211> LENGTH: 28
<212> TYPE: PRT
<213> ORGANISM: Artificial Sequence
<220> FEATURE:
<223> OTHER INFORMATION: Description of Artificial Sequence:  Peptide

<400> SEQUENCE: 13
```

```
Ile His Arg His Leu Cys Thr His Leu Arg Gln Ala Thr Asn Gly Gly
 1               5                  10                  15

Arg Ile Arg Pro Val Ile Ser Val Phe Ala Pro Asp
            20                  25

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence:  Peptide

<400> SEQUENCE: 14

Val Trp Asn Glu Gln Leu
 1               5

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence:  Peptide

<400> SEQUENCE: 15

Arg Arg Asp Asp Gly Thr Val Leu Gly Asp Pro Arg
 1               5                  10

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence:  Peptide

<400> SEQUENCE: 16

Ala Asp Leu Thr Glu Ala Ile
 1               5

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence:  Peptide

<400> SEQUENCE: 17

Leu Gly Trp Gln Gly
 1               5

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence:  Peptide

<400> SEQUENCE: 18

Gln Gly Pro Phe Asp Val Leu Pro Leu Val Ile Asp
 1               5                  10

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence:  Peptide
```

```
<400> SEQUENCE: 19

Asp Asp Lys Pro Arg Phe Phe Glu Leu Pro Arg Glu
 1               5                  10

<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence: Peptide

<400> SEQUENCE: 20

Val Leu Glu Val Pro Ile Thr His Pro Asp Val Pro Arg Leu Ala Glu
 1               5                  10                  15

Leu

<210> SEQ ID NO 21
<211> LENGTH: 18
<212> TYPE: PRT
<213> ORGANISM: Artificial Sequence
<220> FEATURE:
<223> OTHER INFORMATION: Description of Artificial Sequence: Peptide

<400> SEQUENCE: 21

Leu Arg Trp His Ala Val Pro Val Ile Ser Asn Met Arg Leu Arg Ile
 1               5                  10                  15

Gly Gly

<210> SEQ ID NO 22
<211> LENGTH: 17
<212> TYPE: PRT
<213> ORGANISM: Artificial Sequence
<220> FEATURE:
<223> OTHER INFORMATION: Description of Artificial Sequence: Peptide

<400> SEQUENCE: 22

Asp Tyr Pro Leu Ala Pro Phe Asn Gly Trp Tyr Met Gly Thr Glu Ile
 1               5                  10                  15

Gly

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Peptide

<400> SEQUENCE: 23

Arg Asn Leu Val Asp Glu
 1               5

<210> SEQ ID NO 24
<211> LENGTH: 35
<212> TYPE: PRT
<213> ORGANISM: Artificial Sequence
<220> FEATURE:
<223> OTHER INFORMATION: Description of Artificial Sequence: Peptide

<400> SEQUENCE: 24

Leu Pro Ala Val Ala Ala Cys Leu Gln Leu Asp Thr Thr Ser Glu Ser
 1               5                  10                  15

Thr Leu Trp Arg Asp Arg Ala Leu Val Glu Leu Asn Val Ala Val Leu
            20                  25                  30
```

His Ser Phe
        35

<210> SEQ ID NO 25
<211> LENGTH: 20
<212> TYPE: PRT
<213> ORGANISM: Artificial Sequence
<220> FEATURE:
<223> OTHER INFORMATION: Description of Artificial Sequence: Peptide

<400> SEQUENCE: 25

Ala Ala Gly Val Arg Ile Ser Asp His His Glu Glu Ser Arg Arg Phe
 1               5                  10                  15

Leu Ala His Leu
          20

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Peptide

<400> SEQUENCE: 26

Lys Glu Glu Arg Gln Gly Arg Thr Val
 1               5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Peptide

<400> SEQUENCE: 27

Lys Glu Glu Arg Gln Gly Arg Thr Val
 1               5

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Peptide

<400> SEQUENCE: 28

Asp Gln Arg Pro Asn Phe Tyr Pro His Gln
 1               5                  10

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Peptide

<400> SEQUENCE: 29

Thr Gly Thr Tyr Arg His Thr Thr
 1               5

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: Peptide

```
<400> SEQUENCE: 30

Gly Ala Arg Val Ala Trp Arg Asn
 1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence:  Peptide

<400> SEQUENCE: 31

Arg Cys Ile Gly Arg Leu Tyr Trp
 1               5

<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence:  Peptide

<400> SEQUENCE: 32

Val Phe Ala Pro Asp
 1               5

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence:  Peptide

<400> SEQUENCE: 33

Trp Asn Glu Gln Leu
 1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence:  Peptide

<400> SEQUENCE: 34

Pro Phe Asp Val Leu Pro Leu
 1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence:  Peptide

<400> SEQUENCE: 35

Leu Arg Trp His Ala Val Pro
 1               5

<210> SEQ ID NO 36
<211> LENGTH: 13
<212> TYPE: PRT
<213> ORGANISM: Artificial Sequence
<220> FEATURE:
<223> OTHER INFORMATION: Description of Artificial Sequence:  Peptide
```

```
<400> SEQUENCE: 36

Ala Pro Phe Asn Gly Trp Tyr Met Gly Thr Glu Ile Gly
1               5                   10

<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: Peptide

<400> SEQUENCE: 37

Asp Arg Ala Leu Val Glu Leu Asn
1               5

<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence: Peptide

<400> SEQUENCE: 38

Val Leu His Ser Phe
1               5

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Peptide

<400> SEQUENCE: 39

Ala Asp Trp Ser Trp Ile Val Pro Pro
1               5

<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: Peptide

<400> SEQUENCE: 40

Thr Pro Val Phe His Arg
1               5

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Peptide
<220> FEATURE:
<221> NAME/KEY: PEPTIDE
<222> LOCATION: (1)
<223> OTHER INFORMATION: Xaa at position 1 is either Arginine or Lysine
<220> FEATURE:
<221> NAME/KEY: PEPTIDE
<222> LOCATION: (2)
<223> OTHER INFORMATION: Xaa at position 2 is either Methionine or
      Valine
<220> FEATURE:
<221> NAME/KEY: PEPTIDE
<222> LOCATION: (7)
<223> OTHER INFORMATION: Xaa at position 7 is either Serine or Alanine

<400> SEQUENCE: 41
```

```
Xaa Xaa Ala Trp Arg Asn Xaa
  1               5

<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence: Peptide
<220> FEATURE:
<221> NAME/KEY: PEPTIDE
<222> LOCATION: (3)
<223> OTHER INFORMATION: Xaa at position 3 is either Isoleucine or
      Valine
<220> FEATURE:
<221> NAME/KEY: PEPTIDE
<222> LOCATION: (6)
<223> OTHER INFORMATION: Xaa at position 6 is either Leucine or
      Isoleucine

<400> SEQUENCE: 42

Arg Cys Xaa Gly Arg Xaa
  1               5

<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence: Peptide
<220> FEATURE:
<221> NAME/KEY: PEPTIDE
<222> LOCATION: (3)
<223> OTHER INFORMATION: Xaa at position 3 is either Isoleucine or
      Valine

<400> SEQUENCE: 43

Gln Leu Xaa Arg Tyr Ala
  1               5

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence: Peptide

<400> SEQUENCE: 44

Arg Cys Ile Gly Arg
  1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Peptide
<220> FEATURE:
<221> NAME/KEY: PEPTIDE
<222> LOCATION: (4)..(6)
<223> OTHER INFORMATION: Xaa at positions 4-6 can be any amino acid

<400> SEQUENCE: 45

Gly Trp Tyr Xaa Xaa Xaa Glu
  1               5

<210> SEQ ID NO 46
<211> LENGTH: 7
<212> TYPE: PRT
```

```
<213> ORGANISM: Artificial Sequence
<220> FEATURE:
<223> OTHER INFORMATION: Description of Artificial Sequence:  Peptide
<220> FEATURE:
<221> NAME/KEY: PEPTIDE
<222> LOCATION: (4)..(6)
<223> OTHER INFORMATION: Xaa at positions 4-6 can be any amino acid

<400> SEQUENCE: 46

Trp Ser Trp Xaa Xaa Xaa Pro
 1               5

<210> SEQ ID NO 47
<211> LENGTH: 398
<212> TYPE: PRT
<213> ORGANISM: Artificial Sequence
<220> FEATURE:
<223> OTHER INFORMATION: Description of Artificial Sequence:  Peptide
<220> FEATURE:
<221> NAME/KEY: NON_TER
<222> LOCATION: (1)
<223> OTHER INFORMATION: Xaa at position 1 represents from 3 up to 49
      undefined residues that can be any amino acid
<220> FEATURE:
<221> NAME/KEY: UNSURE
<222> LOCATION: (21)..(27)
<223> OTHER INFORMATION: Xaa at positions 21-27 can be any amino acid
<220> FEATURE:
<221> NAME/KEY: UNSURE
<222> LOCATION: (37)..(39)
<223> OTHER INFORMATION: Xaa at positions 37-39 can be any amino acid
<220> FEATURE:
<221> NAME/KEY: UNSURE
<222> LOCATION: (46)
<223> OTHER INFORMATION: Xaa at position 46 can be any amino acid
<220> FEATURE:
<221> NAME/KEY: UNSURE
<222> LOCATION: (63)..(71)
<223> OTHER INFORMATION: Xaa at positions 63-71 can be any amino acid
<220> FEATURE:
<221> NAME/KEY: UNSURE
<222> LOCATION: (92)
<223> OTHER INFORMATION: Xaa at position 92 can be any amino acid
<220> FEATURE:
<221> NAME/KEY: UNSURE
<222> LOCATION: (121)..(126)
<223> OTHER INFORMATION: Xaa at positions 121-126 can be any amino acid
<220> FEATURE:
<221> NAME/KEY: UNSURE
<222> LOCATION: (155)..(162)
<223> OTHER INFORMATION: Xaa at positions 155-162 can be any amino acid
<220> FEATURE:
<221> NAME/KEY: UNSURE
<222> LOCATION: (169)..(174)
<223> OTHER INFORMATION: Xaa at positions 169-174 can be any amino acid
<220> FEATURE:
<221> NAME/KEY: UNSURE
<222> LOCATION: (187)
<223> OTHER INFORMATION: Xaa at position 187 can be any amino acid
<220> FEATURE:
<221> NAME/KEY: UNSURE
<222> LOCATION: (195)..(196)
<223> OTHER INFORMATION: Xaa at positions 195-196 can be any amino acid
<220> FEATURE:
<221> NAME/KEY: UNSURE
<222> LOCATION: (202)..(203)
<223> OTHER INFORMATION: Xaa at positions 202-203 can be any amino acid
<220> FEATURE:
<221> NAME/KEY: UNSURE
<222> LOCATION: (216)..(217)
<223> OTHER INFORMATION: Xaa at positions 216-217 can be any amino acid
<220> FEATURE:
<221> NAME/KEY: UNSURE
<222> LOCATION: (230)
<223> OTHER INFORMATION: Xaa at position 230 can be any amino acid
<220> FEATURE:
<221> NAME/KEY: UNSURE
```

-continued

```
<222> LOCATION: (248)
<223> OTHER INFORMATION: Xaa at position 248 can be any amino acid
<220> FEATURE:
<221> NAME/KEY: UNSURE
<222> LOCATION: (267)
<223> OTHER INFORMATION: Xaa at position 267 can be any amino acid
<220> FEATURE:
<221> NAME/KEY: UNSURE
<222> LOCATION: (285)
<223> OTHER INFORMATION: Xaa at position 285 can be any amino acid
<220> FEATURE:
<221> NAME/KEY: UNSURE
<222> LOCATION: (292)..(296)
<223> OTHER INFORMATION: Xaa at positions 292-296 can be any amino acid
<220> FEATURE:
<221> NAME/KEY: UNSURE
<222> LOCATION: (332)
<223> OTHER INFORMATION: Xaa at position 332 can be any amino acid
<220> FEATURE:
<221> NAME/KEY: UNSURE
<222> LOCATION: (353)
<223> OTHER INFORMATION: Xaa at position 353 can be any amino acid
<220> FEATURE:
<221> NAME/KEY: UNSURE
<222> LOCATION: (362)
<223> OTHER INFORMATION: Xaa at position 362 can be any amino acid
<220> FEATURE:
<221> NAME/KEY: UNSURE
<222> LOCATION: (388)
<223> OTHER INFORMATION: Xaa at position 388 can be any amino acid

<400> SEQUENCE: 47

Xaa Glu Val Ala Leu Gly Pro Ser Leu Pro Ala Pro Ser Pro Thr Ala
 1               5                  10                  15

Cys Pro Ala Leu Xaa Xaa Xaa Xaa Xaa Xaa Pro Val Pro Ser Ala
            20                  25                  30

Glu Pro Ala Thr Xaa Xaa Xaa Cys Gly Val Ala Asp Pro Xaa Glu Ala
        35                  40                  45

Glu Glu Phe Leu Arg Gln Phe His Ala Glu Gln Ser Asp Gln Xaa Xaa
    50                  55                  60

Xaa Xaa Xaa Xaa Xaa Xaa Xaa Gln Val Arg Ala Ala Ile Asp Ala Thr
65                  70                  75                  80

Gly Thr Tyr Arg His Thr Thr Ala Glu Leu Val Xaa Gly Ala Arg Val
                85                  90                  95

Ala Trp Arg Asn Ser Ser Arg Cys Ile Gly Arg Leu Tyr Trp Asn Ser
            100                 105                 110

Leu Arg Val Leu Asp Arg Arg Asp Xaa Xaa Xaa Xaa Xaa Ile His
        115                 120                 125

Arg His Leu Cys Thr His Leu Arg Gln Ala Thr Asn Gly Gly Arg Ile
    130                 135                 140

Arg Pro Val Ile Ser Val Phe Ala Pro Asp Xaa Xaa Xaa Xaa Xaa
145                 150                 155                 160

Xaa Xaa Val Trp Asn Glu Gln Leu Xaa Xaa Xaa Xaa Xaa Arg Arg
                165                 170                 175

Asp Asp Gly Thr Val Leu Gly Asp Pro Arg Xaa Ala Asp Leu Thr Glu
            180                 185                 190

Ala Ile Xaa Xaa Leu Gly Trp Gln Gly Xaa Xaa Gln Gly Pro Phe Asp
        195                 200                 205

Val Leu Pro Leu Val Ile Asp Xaa Xaa Asp Asp Lys Pro Arg Phe Phe
    210                 215                 220

Glu Leu Pro Arg Glu Xaa Val Leu Glu Val Pro Ile Thr His Pro Asp
225                 230                 235                 240

Val Pro Arg Leu Ala Glu Leu Xaa Leu Arg Trp His Ala Val Pro Val
```

-continued

```
                245                 250                 255
Ile Ser Asn Met Arg Leu Arg Ile Gly Gly Xaa Asp Tyr Pro Leu Ala
        260                 265                 270

Pro Phe Asn Gly Trp Tyr Met Gly Thr Glu Ile Gly Xaa Arg Asn Leu
        275                 280                 285

Val Asp Glu Xaa Xaa Xaa Xaa Leu Pro Ala Val Ala Ala Cys Leu
    290                 295                 300

Gln Leu Asp Thr Thr Ser Glu Ser Thr Leu Trp Arg Asp Arg Ala Leu
305                 310                 315                 320

Val Glu Leu Asn Val Ala Val Leu His Ser Phe Xaa Ala Ala Gly Val
                325                 330                 335

Arg Ile Ser Asp His His Glu Glu Ser Arg Arg Phe Leu Ala His Leu
            340                 345                 350

Xaa Lys Glu Glu Arg Gln Gly Arg Thr Val Xaa Ala Asp Trp Ser Trp
        355                 360                 365

Ile Val Pro Pro Leu Ser Gly Gly Ile Thr Pro Val Phe His Arg Tyr
    370                 375                 380

Tyr Asp Asn Xaa Asp Gln Arg Pro Asn Phe Tyr Pro His Gln
385                 390                 395
```

<210> SEQ ID NO 48
<211> LENGTH: 306
<212> TYPE: PRT
<213> ORGANISM: Artificial Sequence
<220> FEATURE:
<223> OTHER INFORMATION: Description of Artificial Sequence:  Peptide
<220> FEATURE:
<221> NAME/KEY: NON_TER
<222> LOCATION: (1)
<223> OTHER INFORMATION: Xaa at position 1 represents from 81 up to 151
      undefined residues that can be any amino acid
<220> FEATURE:
<221> NAME/KEY: UNSURE
<222> LOCATION: (10)..(14)
<223> OTHER INFORMATION: Xaa at positions 10-14 can be any amino acid
<220> FEATURE:
<221> NAME/KEY: UNSURE
<222> LOCATION: (23)..(24)
<223> OTHER INFORMATION: Xaa at positions 23-24 can be any amino acid
<220> FEATURE:
<221> NAME/KEY: UNSURE
<222> LOCATION: (33)..(71)
<223> OTHER INFORMATION: Xaa at positions 33-71 can be any amino acid
<220> FEATURE:
<221> NAME/KEY: UNSURE
<222> LOCATION: (77)..(85)
<223> OTHER INFORMATION: Xaa at positions 77-85 can be any amino acid
<220> FEATURE:
<221> NAME/KEY: UNSURE
<222> LOCATION: (91)..(127)
<223> OTHER INFORMATION: Xaa at positions 91-127 can be any amino acid
<220> FEATURE:
<221> NAME/KEY: UNSURE
<222> LOCATION: (135)..(170)
<223> OTHER INFORMATION: Xaa at positions 135-170 can be any amino acid
<220> FEATURE:
<221> NAME/KEY: UNSURE
<222> LOCATION: (178)..(193)
<223> OTHER INFORMATION: Xaa at positions 178-193 can be any amino acid
<220> FEATURE:
<221> NAME/KEY: UNSURE
<222> LOCATION: (207)..(238)
<223> OTHER INFORMATION: Xaa at positions 207-238 can be any amino acid
<220> FEATURE:
<221> NAME/KEY: UNSURE
<222> LOCATION: (247)..(248)
<223> OTHER INFORMATION: Xaa at positions 247-248 can be any amino acid
<220> FEATURE:
<221> NAME/KEY: UNSURE

```
<222> LOCATION: (254)..(285)
<223> OTHER INFORMATION: Xaa at positions 254-285 can be any amino acid
<220> FEATURE:
<221> NAME/KEY: UNSURE
<222> LOCATION: (295)..(299)
<223> OTHER INFORMATION: Xaa at positions 295-299 can be any amino acid
<220> FEATURE:
<221> NAME/KEY: UNSURE
<222> LOCATION: (306)
<223> OTHER INFORMATION: Xaa at position 306 represents from 15 up to 30
      undefined residues that can be any amino acid

<400> SEQUENCE: 48

Xaa Thr Gly Thr Tyr Arg His Thr Thr Xaa Xaa Xaa Xaa Xaa Gly Ala
 1               5                  10                  15

Arg Val Ala Trp Arg Asn Xaa Xaa Arg Cys Ile Gly Arg Leu Tyr Trp
             20                  25                  30

Xaa Xaa Xaa Xaa Xaa Xaa Xaa Xaa Xaa Xaa Xaa Xaa Xaa Xaa Xaa Xaa
         35                  40                  45

Xaa Xaa Xaa Xaa Xaa Xaa Xaa Xaa Xaa Xaa Xaa Xaa Xaa Xaa Xaa Xaa
 50                  55                  60

Xaa Xaa Xaa Xaa Xaa Xaa Xaa Val Phe Ala Pro Asp Xaa Xaa Xaa Xaa
 65                  70                  75                  80

Xaa Xaa Xaa Xaa Xaa Trp Asn Glu Gln Leu Xaa Xaa Xaa Xaa Xaa Xaa
             85                  90                  95

Xaa Xaa Xaa Xaa Xaa Xaa Xaa Xaa Xaa Xaa Xaa Xaa Xaa Xaa Xaa Xaa
        100                 105                 110

Xaa Xaa Xaa Xaa Xaa Xaa Xaa Xaa Xaa Xaa Xaa Xaa Xaa Xaa Xaa Pro
        115                 120                 125

Phe Asp Val Leu Pro Leu Xaa Xaa Xaa Xaa Xaa Xaa Xaa Xaa Xaa Xaa
130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Leu Arg Trp His Ala Val
                165                 170                 175

Pro Xaa Xaa Xaa Xaa Xaa Xaa Xaa Xaa Xaa Xaa Xaa Xaa Xaa Xaa Xaa
            180                 185                 190

Xaa Ala Pro Phe Asn Gly Trp Tyr Met Gly Thr Glu Ile Gly Xaa Xaa
        195                 200                 205

Xaa Xaa Xaa Xaa Xaa Xaa Xaa Xaa Xaa Xaa Xaa Xaa Xaa Xaa Xaa Xaa
        210                 215                 220

Xaa Xaa Xaa Xaa Xaa Xaa Xaa Xaa Xaa Xaa Xaa Xaa Xaa Xaa Asp Arg
225                 230                 235                 240

Ala Leu Val Glu Leu Asn Xaa Xaa Val Leu His Ser Phe Xaa Xaa Xaa
            245                 250                 255

Xaa Xaa Xaa Xaa Xaa Xaa Xaa Xaa Xaa Xaa Xaa Xaa Xaa Xaa Xaa Xaa
        260                 265                 270

Xaa Xaa Xaa Xaa Xaa Xaa Xaa Xaa Xaa Xaa Xaa Xaa Xaa Ala Asp Trp
        275                 280                 285

Ser Trp Ile Val Pro Pro Xaa Xaa Xaa Xaa Xaa Thr Pro Val Phe His
    290                 295                 300

Arg Xaa
305

<210> SEQ ID NO 49
<211> LENGTH: 23
<212> TYPE: PRT
<213> ORGANISM: Artificial Sequence
```

```
<220> FEATURE:
<223> OTHER INFORMATION: Description of Artificial Sequence:  Peptide
<220> FEATURE:
<221> NAME/KEY: NON_TER
<222> LOCATION: (1)
<223> OTHER INFORMATION: Xaa at position 1 represents from 29 up to 166
      undefined residues that can be any amino acid
<220> FEATURE:
<221> NAME/KEY: UNSURE
<222> LOCATION: (2)
<223> OTHER INFORMATION: Xaa at position 2 can be R or K
<220> FEATURE:
<221> NAME/KEY: UNSURE
<222> LOCATION: (3)
<223> OTHER INFORMATION: Xaa at position 3 can be M or V
<220> FEATURE:
<221> NAME/KEY: UNSURE
<222> LOCATION: (8)
<223> OTHER INFORMATION: Xaa at position 8 can be S or A
<220> FEATURE:
<221> NAME/KEY: UNSURE
<222> LOCATION: (9)
<223> OTHER INFORMATION: Xaa at position 9 can be any amino acid
<220> FEATURE:
<221> NAME/KEY: UNSURE
<222> LOCATION: (12)
<223> OTHER INFORMATION: Xaa at position 12 can be I or V
<220> FEATURE:
<221> NAME/KEY: UNSURE
<222> LOCATION: (15)
<223> OTHER INFORMATION: Xaa at position 15 can be L or I
<220> FEATURE:
<221> NAME/KEY: UNSURE
<222> LOCATION: (16)
<223> OTHER INFORMATION: Xaa at position 16 represents from 52 up to 58
      undefined residues that can be any amino acid
<220> FEATURE:
<221> NAME/KEY: UNSURE
<222> LOCATION: (19)
<223> OTHER INFORMATION: Xaa at position 19 can be I or V
<220> FEATURE:
<221> NAME/KEY: UNSURE
<222> LOCATION: (22)
<223> OTHER INFORMATION: Xaa at position 22 represents from 220 up to
      243 undefined residues that can be any amino acid

<400> SEQUENCE: 49

Xaa Xaa Xaa Ala Trp Arg Asn Xaa Xaa Arg Cys Xaa Gly Arg Xaa Xaa
 1               5                  10                  15

Gln Leu Xaa Arg Tyr Ala Xaa
            20

<210> SEQ ID NO 50
<211> LENGTH: 23
<212> TYPE: PRT
<213> ORGANISM: Artificial Sequence
<220> FEATURE:
<223> OTHER INFORMATION: Description of Artificial Sequence:  Peptide
<220> FEATURE:
<221> NAME/KEY: NON_TER
<222> LOCATION: (1)
<223> OTHER INFORMATION: Xaa at position 1 represents from 37 up to 174
      undefined residues that can be any amino acid
<220> FEATURE:
<221> NAME/KEY: UNSURE
<222> LOCATION: (7)
<223> OTHER INFORMATION: Xaa at position 7 represents from 48 up to 67
      undefined residues that can be any amino acid
<220> FEATURE:
<221> NAME/KEY: UNSURE
<222> LOCATION: (11)..(13)
<223> OTHER INFORMATION: Xaa at positions 11-13 can be any amino acid
<220> FEATURE:
<221> NAME/KEY: UNSURE
<222> LOCATION: (15)
<223> OTHER INFORMATION: Xaa at position 15 represents up to 83
```

-continued

```
      undefined residues that can be any amino acid
<220> FEATURE:
<221> NAME/KEY: UNSURE
<222> LOCATION: (19)..(21)
<223> OTHER INFORMATION: Xaa at positions 19-21 can be any amino acid
<220> FEATURE:
<221> NAME/KEY: UNSURE
<222> LOCATION: (23)
<223> OTHER INFORMATION: Xaa at position 23 represents from 20 up to 38
      undefined residues that can be any amino acid

<400> SEQUENCE: 50

Xaa Arg Cys Ile Gly Arg Xaa Gly Trp Tyr Xaa Xaa Xaa Glu Xaa Trp
 1               5                  10                  15

Ser Trp Xaa Xaa Xaa Pro Xaa
            20

<210> SEQ ID NO 51
<211> LENGTH: 356
<212> TYPE: PRT
<213> ORGANISM: Bacillus anthracis

<400> SEQUENCE: 51

Met Ser Lys Thr Lys Gln Leu Ile Glu Glu Ala Ser His Phe Ile Thr
 1               5                  10                  15

Ile Cys Tyr Lys Glu Leu Ser Lys Glu His Phe Ile Glu Glu Arg Met
            20                  25                  30

Lys Glu Ile Gln Ala Glu Ile Glu Lys Thr Gly Thr Tyr Glu His Thr
        35                  40                  45

Phe Glu Glu Leu Val His Gly Ser Arg Met Ala Trp Arg Asn Ser Asn
 50                  55                  60

Arg Cys Ile Gly Arg Leu Phe Trp Ser Lys Met His Ile Leu Asp Ala
 65                  70                  75                  80

Arg Glu Val Asn Asp Glu Glu Gly Val Tyr His Ala Leu Ile His His
                85                  90                  95

Ile Lys Tyr Ala Thr Asn Asp Gly Lys Val Lys Pro Thr Ile Thr Ile
            100                 105                 110

Phe Lys Gln Tyr Gln Gly Glu Glu Asn Asn Ile Arg Ile Tyr Asn His
        115                 120                 125

Gln Leu Ile Arg Tyr Ala Gly Tyr Lys Thr Glu Met Gly Val Thr Gly
130                 135                 140

Asp Ser His Ser Thr Ala Phe Thr Asp Phe Cys Gln Glu Leu Gly Trp
145                 150                 155                 160

Gln Gly Glu Gly Thr Asn Phe Asp Val Leu Pro Leu Val Phe Ser Ile
                165                 170                 175

Asp Gly Lys Ala Pro Ile Tyr Lys Glu Ile Pro Lys Glu Glu Val Lys
            180                 185                 190

Glu Val Pro Ile Glu His Pro Glu Tyr Pro Ile Ser Ser Leu Gly Ala
        195                 200                 205

Lys Trp Tyr Gly Val Pro Met Ile Ser Asp Met Arg Leu Glu Ile Gly
210                 215                 220

Gly Ile Ser Tyr Thr Ala Ala Pro Phe Asn Gly Trp Tyr Met Gly Thr
225                 230                 235                 240

Glu Ile Gly Ala Arg Asn Leu Ala Asp His Asp Arg Tyr Asn Leu Leu
                245                 250                 255

Pro Ala Val Ala Glu Met Met Asp Leu Asp Thr Ser Arg Asn Gly Thr
            260                 265                 270

Leu Trp Lys Asp Lys Ala Leu Ile Glu Leu Asn Val Ala Val Leu His
```

```
                275                 280                 285
Ser Phe Lys Lys Gln Gly Val Ser Ile Val Asp His His Thr Ala Ala
            290                 295                 300

Gln Gln Phe Gln Gln Phe Glu Lys Gln Glu Ala Ala Cys Gly Arg Val
305                 310                 315                 320

Val Thr Gly Asn Trp Val Trp Leu Ile Pro Pro Leu Ser Pro Ala Thr
                325                 330                 335

Thr His Ile Tyr His Lys Pro Tyr Pro Asn Glu Ile Leu Lys Pro Asn
                340                 345                 350

Phe Phe His Lys
            355

<210> SEQ ID NO 52
<211> LENGTH: 356
<212> TYPE: PRT
<213> ORGANISM: Bacillus cereus

<400> SEQUENCE: 52

Met Ser Lys Thr Lys Gln Leu Ile Glu Glu Ala Ser Asn Phe Ile Thr
1               5                   10                  15

Ile Cys Tyr Lys Glu Leu His Lys Glu Gln Leu Ile Glu Glu Arg Ile
            20                  25                  30

Lys Glu Ile Gln Ile Glu Ile Glu Lys Thr Gly Thr Tyr Glu His Thr
        35                  40                  45

Phe Glu Glu Leu Val His Gly Ser Arg Met Ala Trp Arg Asn Ser Asn
    50                  55                  60

Arg Cys Ile Gly Arg Leu Phe Trp Ser Lys Met His Ile Leu Asp Ala
65                  70                  75                  80

Arg Glu Val Asn Asp Glu Gly Val Tyr Asn Ala Leu Ile His His
                85                  90                  95

Ile Lys Tyr Ala Thr Asn Asp Gly Lys Val Lys Pro Thr Ile Thr Ile
            100                 105                 110

Phe Lys Gln Tyr Gln Gly Glu Glu Asn Asn Ile Arg Ile Tyr Asn His
        115                 120                 125

Gln Leu Ile Arg Tyr Ala Gly Tyr Lys Thr Glu Thr Gly Val Ile Gly
    130                 135                 140

Asp Ser His Ser Ala Thr Phe Thr Asp Phe Cys Gln Gly Leu Gly Trp
145                 150                 155                 160

Gln Gly Glu Gly Thr Asn Phe Asp Val Leu Pro Leu Val Phe Ser Ile
                165                 170                 175

Asn Gly Lys Ala Pro Thr Tyr Lys Glu Ile Pro Arg Glu Glu Val Lys
            180                 185                 190

Glu Val Pro Ile Glu His Pro Glu Tyr Pro Ile Ser Ser Leu Gly Val
        195                 200                 205

Lys Trp Tyr Gly Val Pro Met Ile Ser Asp Met Arg Leu Glu Ile Gly
    210                 215                 220

Gly Ile Ser Tyr Thr Ala Ala Pro Phe Asn Gly Trp Tyr Met Gly Thr
225                 230                 235                 240

Glu Ile Gly Ala Arg Asn Leu Ala Asp His Asp Arg Tyr Asn Leu Leu
                245                 250                 255

Pro Ala Val Ala Glu Met Met Asp Leu Asp Thr Ser Arg Asn Gly Thr
            260                 265                 270

Leu Trp Lys Asp Lys Ala Leu Ile Glu Leu Asn Ile Ala Val Leu His
        275                 280                 285
```

```
Ser Phe Lys Lys Gln Gly Val Ser Ile Val Asp His His Thr Ala Ala
    290                 295                 300

Gln Gln Phe Gln Gln Phe Glu Lys Gln Glu Ala Ala Cys Gly Arg Val
305                 310                 315                 320

Val Thr Gly Asn Trp Val Trp Leu Ile Pro Pro Leu Ser Pro Ala Thr
                325                 330                 335

Thr His Ile Tyr His Lys Pro Tyr Pro Asn Glu Ile Leu Lys Pro Asn
            340                 345                 350

Phe Phe His Lys
        355

<210> SEQ ID NO 53
<211> LENGTH: 358
<212> TYPE: PRT
<213> ORGANISM: Staphylococcus aureus

<400> SEQUENCE: 53

Met Leu Phe Lys Glu Ala Gln Ala Phe Ile Glu Asn Met Tyr Lys Glu
1               5                   10                  15

Cys His Tyr Glu Thr Gln Ile Ile Asn Lys Arg Leu His Asp Ile Glu
            20                  25                  30

Leu Glu Ile Lys Glu Thr Gly Thr Tyr Thr His Thr Glu Glu Glu Leu
        35                  40                  45

Ile Tyr Gly Ala Lys Met Ala Trp Arg Asn Ser Asn Arg Cys Ile Gly
    50                  55                  60

Arg Leu Phe Trp Asp Ser Leu Asn Val Ile Asp Ala Arg Asp Val Thr
65                  70                  75                  80

Asp Glu Ala Ser Phe Leu Ser Ser Ile Thr Tyr His Ile Thr Gln Ala
                85                  90                  95

Thr Asn Glu Gly Lys Leu Lys Pro Tyr Ile Thr Ile Tyr Ala Pro Lys
            100                 105                 110

Asp Gly Pro Lys Ile Phe Asn Asn Gln Leu Ile Arg Tyr Ala Gly Tyr
        115                 120                 125

Asp Asn Cys Gly Asp Pro Ala Glu Lys Glu Val Thr Arg Leu Ala Asn
130                 135                 140

His Leu Gly Trp Lys Gly Lys Gly Thr Asn Phe Asp Val Leu Pro Leu
145                 150                 155                 160

Ile Tyr Gln Leu Pro Asn Glu Ser Val Lys Phe Tyr Glu Tyr Pro Thr
                165                 170                 175

Ser Leu Ile Lys Glu Val Pro Ile Glu His Asn His Tyr Pro Lys Leu
            180                 185                 190

Arg Lys Leu Asn Leu Lys Trp Tyr Ala Val Pro Ile Ile Ser Asn Met
        195                 200                 205

Asp Leu Lys Ile Gly Gly Ile Val Tyr Pro Thr Ala Pro Phe Asn Gly
    210                 215                 220

Trp Tyr Met Val Thr Glu Ile Gly Val Arg Asn Phe Ile Asp Asp Tyr
225                 230                 235                 240

Arg Tyr Asn Leu Leu Glu Lys Val Ala Asp Ala Phe Glu Phe Asp Thr
                245                 250                 255

Leu Lys Asn Asn Ser Phe Asn Lys Asp Arg Ala Leu Val Glu Leu Asn
            260                 265                 270

Tyr Ala Val Tyr His Ser Phe Lys Lys Glu Gly Val Ser Ile Val Asp
        275                 280                 285

His Leu Thr Ala Ala Lys Gln Phe Glu Leu Phe Glu Arg Asn Glu Ala
    290                 295                 300
```

```
Gln Gln Gly Arg Gln Val Thr Gly Lys Trp Ser Trp Leu Ala Pro Pro
305                 310                 315                 320

Leu Ser Pro Thr Leu Thr Ser Asn Tyr His His Gly Tyr Asp Asn Thr
            325                 330                 335

Val Lys Asp Pro Asn Phe Phe Tyr Lys Lys Glu Ser Asn Ala Asn
        340                 345                 350

Gln Cys Pro Phe His His
        355

<210> SEQ ID NO 54
<211> LENGTH: 355
<212> TYPE: PRT
<213> ORGANISM: Staphylococcus epidermidis

<400> SEQUENCE: 54

Met Leu Ile Asp Lys Ala Arg Ser Phe Ile Gln Thr Met Tyr Ser Glu
1               5                   10                  15

Leu Lys Tyr Asn Thr Asn Glu Ile Glu Asn Arg Met Lys Glu Ile Glu
            20                  25                  30

Gln Glu Ile Asn Leu Thr Gly Ser Tyr Thr His Thr Tyr Glu Glu Leu
        35                  40                  45

Ser Tyr Gly Ala Lys Met Ala Trp Arg Asn Ser Asn Arg Cys Ile Gly
    50                  55                  60

Arg Leu Phe Trp Asn Ser Leu Asn Val Lys Asp Ala Arg Asp Val Cys
65                  70                  75                  80

Asp Glu Lys Glu Phe Ile Lys Phe Ile His Thr Ile Lys Glu Ala
                85                  90                  95

Thr Asn Gly Gly Lys Ile Lys Pro Tyr Ile Thr Ile Phe Ser Pro Glu
            100                 105                 110

Asp Thr Pro Lys Ile Tyr Asn Asn Gln Leu Ile Arg Tyr Ala Gly Tyr
        115                 120                 125

Glu Asn Val Gly Asp Pro Ser Glu Lys Lys Val Thr Arg Leu Ala Glu
130                 135                 140

His Leu Gly Trp Lys Gly Lys Gly Ser Asn Phe Asp Ile Leu Pro Leu
145                 150                 155                 160

Ile Tyr Gln Leu Pro Asn Asp Thr Ile Lys Ile His Glu Leu Pro Asn
                165                 170                 175

Asp Ile Val Lys Glu Val Ser Ile His His Glu His Tyr Pro Lys Leu
            180                 185                 190

Ser Lys Leu Gly Leu Lys Trp Tyr Ala Val Pro Ile Ile Ser Asn Met
        195                 200                 205

Asp Leu Lys Ile Gly Gly Ile Thr Tyr Pro Thr Ala Pro Phe Asn Gly
210                 215                 220

Trp Tyr Met Val Thr Glu Ile Ala Val Arg Asn Phe Thr Asp Thr Tyr
225                 230                 235                 240

Arg Tyr Asn Leu Leu Glu Lys Val Ala Glu Ala Phe Glu Phe Asp Thr
                245                 250                 255

Leu Lys Asn Asn Ser Phe Asn Lys Asp Arg Ala Leu Val Glu Leu Asn
            260                 265                 270

His Ala Val Tyr His Ser Phe Lys Ala Asp Gly Val Ser Ile Val Asp
        275                 280                 285

His Leu Thr Ala Ala Lys Gln Phe Glu Met Phe Glu Arg Asn Glu His
290                 295                 300

Gln Gln Asn Arg Asn Val Thr Gly Lys Trp Ser Trp Leu Ala Pro Pro
```

-continued

```
                305                 310                 315                 320
Leu Ser Pro Thr Leu Thr Ser Asn Tyr His His Gly Tyr Asp Asn Thr
                    325                 330                 335
Met His His Thr Asn Phe Phe Tyr Lys Lys Glu Glu Pro Met Lys Cys
                340                 345                 350
Pro Phe His
        355

<210> SEQ ID NO 55
<211> LENGTH: 366
<212> TYPE: PRT
<213> ORGANISM: Bacillus halodurans

<400> SEQUENCE: 55

Met Glu Glu Lys Glu Arg Leu Gln Leu Glu Ala Ser Phe Leu Thr
 1               5                  10                  15
Lys Cys Tyr Glu Glu Leu Gly Ser Thr Gly Glu Leu Ser Lys Arg Leu
                20                  25                  30
Glu Glu Val Arg Lys Glu Ile Asp Lys Thr Gly Thr Tyr Val His Thr
            35                  40                  45
Thr Lys Glu Leu Ala His Gly Ala Arg Met Ala Trp Arg Asn Ser Asn
        50                  55                  60
Arg Cys Ile Gly Arg Leu Phe Trp Glu Ser Leu His Val Leu Asp Cys
65                  70                  75                  80
Arg His Leu Gln Thr Glu Glu Met Ala Glu Ala Leu Val Asp His
                85                  90                  95
Ile Thr Tyr Ala Thr Asn Asp Gly Lys Ile Leu Pro Thr Ile Ser Val
                100                 105                 110
Phe Arg Pro Arg His Pro Asn Lys Gly Asp Val Arg Ile Trp Asn Gln
            115                 120                 125
Gln Leu Ile Arg Tyr Ala Gly Tyr Glu Glu Gly Asp Gln Val Ile Gly
        130                 135                 140
Asp Pro Ile Ser Thr Lys Phe Thr Gln Ala Cys Glu Arg Leu Gly Trp
145                 150                 155                 160
Ser Gly Glu Arg Thr Pro Phe Asp Val Leu Pro Leu Val Ile Gln Asp
                165                 170                 175
Gly Ser Lys Pro Pro Lys Trp Phe Ala Val Pro Asn Glu Ser Val Lys
            180                 185                 190
Glu Val Pro Leu Arg His Pro Glu Tyr Glu Trp Phe Ala Gly Phe Gln
        195                 200                 205
Leu Lys Trp Tyr Ala Val Pro Ile Val Ser Asn Met Arg Leu Glu Ile
    210                 215                 220
Gly Gly Ile His Tyr Pro Ala Ala Phe Asn Gly Trp Tyr Met Gly
225                 230                 235                 240
Thr Glu Ile Gly Ala Arg Asn Leu Ala Asp Glu Asp Arg Tyr Asn Ile
                245                 250                 255
Leu Pro Lys Met Ala Glu Tyr Met Gly Leu Ser Thr Gly Lys Asp Ser
            260                 265                 270
Thr Leu Trp Lys Asp Lys Ala Leu Val Glu Leu Asn Val Ala Ile Leu
        275                 280                 285
Tyr Ser Tyr Lys Gln Glu Gly Val Ser Ile Val Asp His His Thr Ala
    290                 295                 300
Ala Lys Gln Phe Ala Arg Phe Glu Gln Ala Glu Gln Ala Ala Asn Arg
305                 310                 315                 320
```

-continued

Lys Val Thr Gly Arg Trp Ser Trp Leu Ile Pro Pro Val Ser Pro Ala
                325                 330                 335

Thr Thr His Ile Phe His His Glu Tyr Glu Asp Glu Thr Val Leu Pro
            340                 345                 350

Asn Tyr Phe Tyr Gln Pro Ala Pro Tyr Glu Ser Asp Thr Phe
        355                 360                 365

<210> SEQ ID NO 56
<211> LENGTH: 344
<212> TYPE: PRT
<213> ORGANISM: Bacillus subtilis

<400> SEQUENCE: 56

Met Lys Asp Arg Leu Ala Asp Ile Lys Ser Glu Ile Asp Leu Thr Gly
 1               5                  10                  15

Ser Tyr Val His Thr Lys Glu Leu Glu His Gly Ala Lys Met Ala
             20                  25                  30

Trp Arg Asn Ser Asn Arg Cys Ile Gly Arg Leu Phe Trp Asn Ser Leu
         35                  40                  45

Asn Val Ile Asp Arg Arg Asp Val Arg Thr Lys Glu Glu Val Arg Asp
     50                  55                  60

Ala Leu Phe His His Ile Glu Thr Ala Thr Asn Asn Gly Lys Ile Arg
 65                  70                  75                  80

Pro Thr Ile Thr Ile Phe Pro Pro Glu Glu Lys Gly Glu Lys Gln Val
                 85                  90                  95

Glu Ile Trp Asn His Gln Leu Ile Arg Tyr Ala Gly Tyr Glu Ser Asp
             100                 105                 110

Gly Glu Arg Ile Gly Asp Pro Ala Ser Cys Ser Leu Thr Ala Ala Cys
         115                 120                 125

Glu Glu Leu Gly Trp Arg Gly Glu Arg Thr Asp Phe Asp Leu Leu Pro
    130                 135                 140

Leu Ile Phe Arg Met Lys Gly Asp Glu Gln Pro Val Trp Tyr Glu Leu
145                 150                 155                 160

Pro Arg Ser Leu Val Ile Glu Val Pro Ile Thr His Pro Asp Ile Glu
                165                 170                 175

Ala Phe Ser Asp Leu Glu Leu Lys Trp Tyr Gly Val Pro Ile Ile Ser
            180                 185                 190

Asp Met Lys Leu Glu Val Gly Gly Ile His Tyr Asn Ala Ala Pro Phe
        195                 200                 205

Asn Gly Trp Tyr Met Gly Thr Glu Ile Gly Ala Arg Asn Leu Ala Asp
    210                 215                 220

Glu Lys Arg Tyr Asp Lys Leu Lys Val Ala Ser Val Ile Gly Ile
225                 230                 235                 240

Ala Ala Asp Tyr Asn Thr Asp Leu Trp Lys Asp Gln Ala Leu Val Glu
                245                 250                 255

Leu Asn Lys Ala Val Leu His Ser Tyr Lys Lys Gln Gly Val Ser Ile
            260                 265                 270

Val Asp His His Thr Ala Ala Ser Gln Phe Lys Arg Phe Glu Glu Gln
        275                 280                 285

Glu Glu Glu Ala Gly Arg Lys Leu Thr Gly Asp Trp Thr Trp Leu Ile
    290                 295                 300

Pro Pro Ile Ser Pro Ala Ala Thr His Ile Phe His Arg Ser Tyr Asp
305                 310                 315                 320

Asn Ser Ile Val Lys Pro Asn Tyr Phe Tyr Gln Asp Lys Pro Tyr Glu
                325                 330                 335

Asx Thr Thr Met Phe Phe Arg Met
              340

<210> SEQ ID NO 57
<211> LENGTH: 356
<212> TYPE: PRT
<213> ORGANISM: Deinococcus radiodurans

<400> SEQUENCE: 57

Met Ser Cys Pro Ala Ala Val Leu Thr Pro Asp Met Arg Ala Phe
  1               5                  10                  15

Leu Arg Arg Phe His Glu Glu Met Gly Glu Pro Gly Leu Pro Ala Arg
                 20                  25                  30

Leu Arg Ala Val Glu Glu Ala Gly Leu Trp Trp Pro Thr Ser Ala Glu
             35                  40                  45

Leu Thr Trp Gly Ala Lys Val Ala Trp Arg Asn Ser Thr Arg Cys Val
 50                  55                  60

Gly Arg Leu Tyr Trp Glu Ala Leu Ser Val Arg Asp Leu Arg Glu Leu
 65                  70                  75                  80

Asn Thr Ala Gln Ala Val Tyr Glu Ala Leu Leu Gln His Leu Asp Asp
                 85                  90                  95

Ala Phe Cys Gly Gly His Ile Arg Pro Val Ile Ser Val Phe Gly Pro
            100                 105                 110

Gly Val Arg Leu His Asn Pro Gln Leu Ile Arg Tyr Ala Asp Asp Pro
        115                 120                 125

Ile Asn Ala Asp Phe Val Asp Lys Leu Arg Arg Phe Gly Trp Gln Pro
130                 135                 140

Arg Gly Glu Arg Phe Glu Val Leu Pro Leu Leu Ile Glu Val Asn Gly
145                 150                 155                 160

Arg Ala Glu Leu Phe Ser Leu Pro Pro Gln Ala Val Gln Glu Val Ala
                165                 170                 175

Ile Thr His Pro Val Cys Leu Gly Ile Gly Glu Leu Gly Leu Arg Trp
            180                 185                 190

His Ala Leu Pro Val Ile Ser Asp Met His Leu Asp Ile Gly Gly Leu
        195                 200                 205

His Leu Pro Cys Ala Phe Ser Gly Trp Tyr Val Gln Thr Glu Ile Ala
210                 215                 220

Ala Arg Asp Leu Ala Asp Val Gly Arg Tyr Asp Gln Leu Pro Ala Val
225                 230                 235                 240

Ala Arg Ala Leu Gly Leu Asp Thr Ser Arg Glu Arg Thr Leu Trp Arg
                245                 250                 255

Asp Arg Ala Leu Val Glu Leu Asn Val Ala Val Leu His Ser Phe Asp
            260                 265                 270

Ala Ala Gly Val Lys Leu Ala Asp His His Thr Val Thr Ala His His
        275                 280                 285

Val Arg Phe Glu Glu Arg Glu Ala Arg Ala Gly Arg Glu Val Arg Gly
    290                 295                 300

Lys Trp Ser Trp Leu Val Pro Pro Leu Ser Pro Ala Thr Thr Pro Leu
305                 310                 315                 320

Trp Ser Arg Arg Tyr Arg Ala Arg Glu Glu Ser Pro Arg Phe Val Arg
                325                 330                 335

Ala Arg Cys Pro Phe His Thr Pro Thr Val His Ala Ser Thr Gly His
            340                 345                 350

Ala Pro Thr Gly

-continued

<210> SEQ ID NO 58
<211> LENGTH: 485
<212> TYPE: PRT
<213> ORGANISM: Streptomyces avermitilis

<400> SEQUENCE: 58

```
Leu Ala Asp Ala Pro Pro Glu Ser Ala Ala Ser Arg Pro Gly Gly Asp
 1               5                  10                  15

Ala Arg Asp Arg His Gly Ala Pro Ser Arg Ala Arg Gly Trp Ser Thr
            20                  25                  30

Glu Thr Trp Cys Ala Pro His Gly Arg Lys Asp Thr Ala Gly Glu Ser
        35                  40                  45

Glu His Arg Pro Pro Gly Pro Thr Leu Pro Gly Ala Arg Gly Trp Gly
    50                  55                  60

Ala Ala Arg Thr Arg Gly Asp Arg Pro Asp Gly His Pro Asp His Pro
65                  70                  75                  80

Thr Gly Ser Pro Thr Thr Asp Gly Pro Ala Arg Pro Ala Arg Pro Asp
                85                  90                  95

Arg Arg Glu Glu Gly Asp Gly His Asp Gly His Glu Gly Gln Asp Gly
            100                 105                 110

His Asp Gly His Asp Leu Leu Cys Ala Ala Thr Ala Phe Leu Thr Leu
        115                 120                 125

His His Thr Glu Glu Arg Leu Gly Asp Pro Ala Arg Arg Ile Ala Ala
    130                 135                 140

Ala His Ala Glu Ile Ala Glu Thr Gly Thr Tyr Arg His Thr Thr Glu
145                 150                 155                 160

Glu Leu Val Phe Gly Ala Arg Val Ala Trp Arg Asn Ala Asn Arg Cys
                165                 170                 175

Ile Gly Arg Leu Tyr Trp His Ser Leu Cys Val Arg Asp Arg Arg Asp
            180                 185                 190

Val Arg Asp Ala Lys Asp Val Ala Glu Ala Ser Ala Asp His Leu Arg
        195                 200                 205

Glu Ala Thr Arg Asp Gly Arg Ile Arg Ala Leu Ile Thr Val Phe Ala
    210                 215                 220

Pro Asp Ala Pro Gly Arg Pro Gly Pro Arg Ile Trp Asn Glu Gln Leu
225                 230                 235                 240

Ile Arg Tyr Ala Gly Tyr Ala Arg Pro Gly Gly Ala Val Thr Gly Asp
                245                 250                 255

Pro Arg Asn Ala Gly Leu Thr Ala Leu Ala Arg Arg Leu Gly Trp Pro
            260                 265                 270

Gly Gly Pro Gly Ser Pro Phe Asp Val Leu Pro Leu Ile Val Gln Ser
        275                 280                 285

Ala Gly Asp Arg Pro Arg Trp Phe Thr Leu Pro Glu Asp Ala Val Leu
    290                 295                 300

Glu Val Ala Leu Thr His Pro Glu Tyr Pro Trp Trp Arg Ser Leu Gly
305                 310                 315                 320

Leu Arg Trp His Ala Val Pro Ala Leu Ala Gly Met Cys Leu Glu Ser
                325                 330                 335

Gly Gly Ile Cys Tyr Pro Ala Ala Pro Phe Asn Gly Trp Tyr Met Gly
            340                 345                 350

Thr Glu Ile Gly Ala Arg Asn Leu Ala Asp Ala Asp Arg Tyr Asp Leu
        355                 360                 365
```

-continued

```
Leu Pro His Leu Ala Asp Arg Leu Gly Leu Asp Thr Arg Ser Asp Arg
    370                 375                 380

Ser Leu Trp Lys Asp Arg Ala Leu Val Glu Leu Asn Arg Ser Val Leu
385                 390                 395                 400

His Ser Phe Asp Arg Ala Gly Val Thr Val Thr Asp His His Thr Glu
                405                 410                 415

Ser Leu Arg Phe Leu Thr His Leu Asp Arg Glu Glu Arg Lys Gly Arg
            420                 425                 430

Arg Val Gly Ala Asp Trp Ser Trp Ile Val Pro Pro Ile Ser Gly Ser
        435                 440                 445

Ala Thr Pro Val Phe His Arg Thr Tyr Glu Thr Val Glu Arg His Pro
    450                 455                 460

Ala Tyr Val His His Pro Glu Ala Leu Ala Arg Ala Arg Gly Glu Ile
465                 470                 475                 480

Asp Glu Ile Leu Val
                485

<210> SEQ ID NO 59
<211> LENGTH: 423
<212> TYPE: PRT
<213> ORGANISM: Mus musculus

<400> SEQUENCE: 59

Gln Tyr Val Arg Ile Lys Asn Trp Gly Ser Gly Glu Ile Leu His Asp
  1               5                  10                  15

Thr Leu His His Lys Ala Thr Ser Asp Phe Thr Cys Lys Ser Lys Ser
                 20                  25                  30

Cys Leu Gly Ser Ile Met Asn Pro Lys Ser Leu Thr Arg Gly Pro Arg
             35                  40                  45

Asp Lys Pro Thr Pro Leu Glu Glu Leu Leu Pro His Ala Ile Glu Phe
         50                  55                  60

Ile Asn Gln Tyr Tyr Gly Ser Phe Lys Glu Ala Lys Ile Glu Glu His
 65                  70                  75                  80

Leu Ala Arg Leu Glu Ala Val Thr Lys Glu Ile Glu Thr Thr Gly Thr
                 85                  90                  95

Tyr Gln Leu Thr Leu Asp Glu Leu Ile Phe Ala Thr Lys Met Ala Trp
            100                 105                 110

Arg Asn Ala Pro Arg Cys Ile Gly Arg Ile Gln Trp Ser Asn Leu Gln
        115                 120                 125

Val Phe Asp Ala Arg Asn Cys Ser Thr Ala Gln Glu Met Phe Gln His
    130                 135                 140

Ile Cys Arg His Ile Leu Tyr Ala Thr Asn Asn Gly Asn Ile Arg Ser
145                 150                 155                 160

Ala Ile Thr Val Phe Pro Gln Arg Ser Asp Gly Lys His Asp Phe Arg
                165                 170                 175

Leu Trp Asn Ser Gln Leu Ile Arg Tyr Ala Gly Tyr Gln Met Pro Asp
            180                 185                 190

Gly Thr Ile Arg Gly Asp Ala Ala Thr Leu Glu Phe Thr Gln Leu Cys
        195                 200                 205

Ile Asp Leu Gly Trp Lys Pro Arg Tyr Gly Arg Phe Asp Val Leu Pro
    210                 215                 220

Leu Val Leu Gln Ala Asp Gly Gln Asp Pro Glu Val Phe Glu Ile Pro
225                 230                 235                 240

Pro Asp Leu Val Leu Glu Val Thr Met Glu His Pro Lys Tyr Glu Trp
                245                 250                 255
```

-continued

```
Phe Gln Glu Leu Gly Leu Lys Trp Tyr Ala Leu Pro Ala Val Ala Asn
            260                 265                 270

Met Leu Leu Glu Val Gly Gly Leu Glu Phe Pro Ala Cys Pro Phe Asn
            275                 280                 285

Gly Trp Tyr Met Gly Thr Glu Ile Gly Val Arg Asp Phe Cys Asp Thr
    290                 295                 300

Gln Arg Tyr Asn Ile Leu Glu Gly Val Gly Arg Arg Met Gly Leu Glu
305                 310                 315                 320

Thr His Thr Leu Ala Ser Leu Trp Lys Asp Arg Ala Val Thr Glu Ile
                325                 330                 335

Asn Val Ala Val Leu His Ser Phe Gln Lys Gln Asn Val Thr Ile Met
                340                 345                 350

Asp His His Thr Ala Ser Glu Ser Phe Met Lys His Met Gln Asn Glu
            355                 360                 365

Tyr Arg Ala Arg Gly Gly Cys Pro Ala Asp Trp Ile Trp Leu Val Pro
    370                 375                 380

Pro Val Ser Gly Ser Ile Thr Pro Val Phe His Gln Glu Met Leu Asn
385                 390                 395                 400

Tyr Val Leu Ser Pro Phe Tyr Tyr Tyr Gln Ile Glu Pro Trp Lys Thr
                405                 410                 415

His Ile Trp Gln Asn Glu Lys
                420
```